United States Patent
Takahashi et al.

(10) Patent No.: US 11,490,963 B2
(45) Date of Patent: *Nov. 8, 2022

(54) ROUTE SELECTION ASSISTANCE SYSTEM, RECORDING MEDIUM ON WHICH ROUTE SELECTION ASSISTANCE PROGRAM IS RECORDED, ROUTE SELECTION ASSISTANCE METHOD, AND DIAGNOSIS METHOD

(71) Applicant: TERUMO KABUSHIKI KAISHA, Tokyo (JP)

(72) Inventors: Haruhiko Takahashi, Tokyo (JP); Yusuke Sekine, Chigasaki (JP); Tetsuya Fukuoka, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 532 days.

This patent is subject to a terminal disclaimer.

(21) Appl. No.: 16/695,737

(22) Filed: Nov. 26, 2019

(65) Prior Publication Data
US 2020/0093543 A1  Mar. 26, 2020

Related U.S. Application Data

(63) Continuation of application No. PCT/JP2018/020531, filed on May 29, 2018.

(30) Foreign Application Priority Data

Jun. 2, 2017  (JP) .............................. JP2017-110379

(51) Int. Cl.
*A61B 34/10* (2016.01)
*A61B 90/00* (2016.01)
(Continued)

(52) U.S. Cl.
CPC .......... *A61B 34/10* (2016.02); *A61B 1/00009* (2013.01); *A61B 5/02007* (2013.01);
(Continued)

(58) Field of Classification Search
CPC .......... A61B 1/00009; A61B 1/000096; A61B 2017/00778; A61B 2034/104;
(Continued)

(56) References Cited

U.S. PATENT DOCUMENTS

2008/0097165 A1  4/2008  Gattani et al.
2008/0183073 A1  7/2008  Higgins et al.
(Continued)

FOREIGN PATENT DOCUMENTS

JP  2000113086 A  4/2000
JP  2009511155 A  3/2009
(Continued)

OTHER PUBLICATIONS

The extended European Search Report dated Feb. 4, 2021, by the European Patent Office in corresponding European Patent Application No. 18810086.1-1122. (15 pages).
(Continued)

*Primary Examiner* — Manuchehr Rahmjoo
(74) *Attorney, Agent, or Firm* — Buchanan Ingersoll & Rooney PC

(57) ABSTRACT

A route selection assistance system, a recording medium on which a route selection assistance program is recorded, a route selection assistance method, and a diagnosis method that enable easy selection of a route of a living body lumen for delivering a medical instrument to a site within a living body via the living body lumen. A route selection assistance system includes: a receiving section configured to receive an input of site information specifying a target site; an image obtaining section configured to obtain image information on
(Continued)

a living body of a target patient; a route extracting section configured to extract a plurality of routes of a living body lumen; a ranking assigning section configured to assign rankings to the plurality of routes extracted by the route extracting section; and an output section configured to output the plurality of routes extracted and the rankings assigned by the ranking assigning section.

14 Claims, 18 Drawing Sheets

(51) Int. Cl.
*A61B 1/00* (2006.01)
*A61B 5/02* (2006.01)
*G06T 19/00* (2011.01)
(52) U.S. Cl.
CPC ............ *A61B 90/36* (2016.02); *G06T 19/003* (2013.01); *A61B 2034/104* (2016.02); *A61B 2034/105* (2016.02); *A61B 2034/107* (2016.02); *G06T 2207/30104* (2013.01)
(58) Field of Classification Search
CPC ........ A61B 2034/105; A61B 2034/107; A61B 2034/256; A61B 2090/3735; A61B 2090/3784; A61B 34/10; A61B 34/20; A61B 5/02007; A61B 6/00; A61B 6/03; A61B 90/36; A61M 25/06; G06T 19/003; G06T 2207/30104
See application file for complete search history.

(56) References Cited

U.S. PATENT DOCUMENTS

| 2008/0234700 | A1 | | 9/2008 | Trovato et al. |
| 2015/0119966 | A1 | | 4/2015 | Richter et al. |
| 2015/0282887 | A1 | | 10/2015 | Yamada |
| 2016/0106512 | A1 | | 4/2016 | Biffi et al. |
| 2018/0085167 | A1 | * | 3/2018 | Goyal .................... A61B 34/10 |

FOREIGN PATENT DOCUMENTS

| JP | 2010517633 A | 5/2010 |
| JP | 2012200403 A | 10/2012 |
| JP | 2014124218 A | 7/2014 |
| JP | 2014230710 A | 12/2014 |
| WO | 2016/083927 A1 | 6/2016 |

OTHER PUBLICATIONS

International Search Report (PCT/ISA/210) dated Jul. 24, 2018, by the Japan Patent Office as the International Searching Authority for International Application No. PCT/JP2018/020531.
Written Opinion (PCT/ISA/237) dated Jul. 24, 2018, by the Japan Patent Office as the International Searching Authority for International Application No. PCT/JP2018/020531.

* cited by examiner

```
SITE INFORMATION INPUT SCREEN

TARGET SITE    [ LEFT SUPERFICIAL  ▼ ]
                 FEMORAL ARTERY
```

| INTRODUCTION SITE | INVASION DEGREE |
|---|---|
| RIGHT RADIAL ARTERY | LOW |
| RIGHT BRACHIAL ARTERY | MEDIUM |
| RIGHT FEMORAL ARTERY | HIGH |
| LEFT RADIAL ARTERY | LOW |
| LEFT BRACHIAL ARTERY | MEDIUM |
| LEFT FEMORAL ARTERY | |

| DIVIDED IMAGE ID | SITE INFORMATION | LINK INFORMATION |
|---|---|---|
| DIVIDED IMAGE 1 | SITE 1 | LINK INFORMATION 1 |
| DIVIDED IMAGE 2 | SITE 2 | LINK INFORMATION 2 |

PROCEDURE INFORMATION INPUT SCREEN

KIND OF PROCEDURE | EXPANSION OF CONSTRICTION ▼

| KIND OF PROCEDURE | KIND OF MEDICAL INSTRUMENT | | |
|---|---|---|---|
| PROCEDURE 1 | MEDICAL INSTRUMENT 1A | MEDICAL INSTRUMENT 1B | MEDICAL INSTRUMEN |
| PROCEDURE 2 | MEDICAL INSTRUMENT 2A | MEDICAL INSTRUMENT 2B | MEDICAL INSTRUMENT |
| PROCEDURE 3 | MEDICAL INSTRUMENT 3A | | |

| MEDICAL INSTRUMENT | DEVICE | | |
|---|---|---|---|
| MEDICAL INSTRUMENT 1A | DEVICE 1Aa | DEVICE 1Ab | DEVICE 1Ac |
| MEDICAL INSTRUMENT 1B | DEVICE 1Ba | DEVICE 1Bb | DEVICE 1Bc |
| MEDICAL INSTRUMENT 2A | DEVICE 2Aa | DEVICE 2Ab | DEVICE 2Ac |

| DEVICE | PRESENCE OR ABSENCE OF STOCK |
|---|---|
| DEVICE 1Aa | PRESENT |
| DEVICE 1Ab | ABSENT |
| DEVICE 2Ba | PRESENT |
| DEVICE 2Bb | |

FIG.14
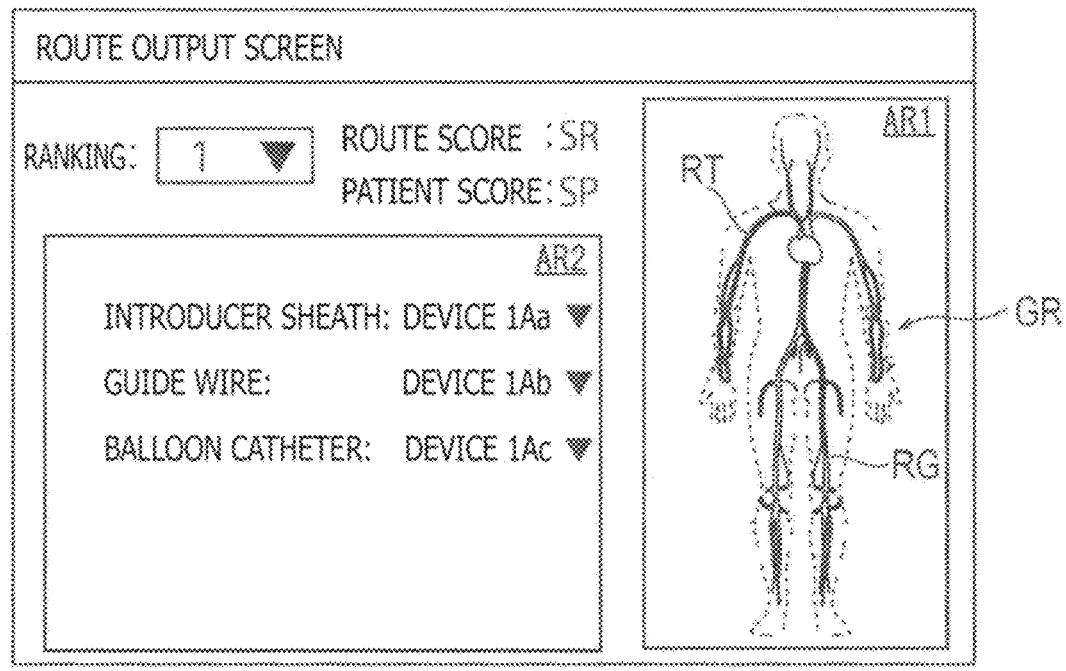
FIG.15
| DEVICE | DEVICE CHARACTERISTIC INFORMATION |
|---|---|
| DEVICE 1Aa | DEVICE CHARACTERISTIC INFORMATION 1Aa |
| DEVICE 1Ab | DEVICE CHARACTERISTIC INFORMATION 1Ab |
| DEVICE 2Ba | DEVICE CHARACTERISTIC INFORMATION 2Ba |
| DEVICE 2Bb | |
FIG.16
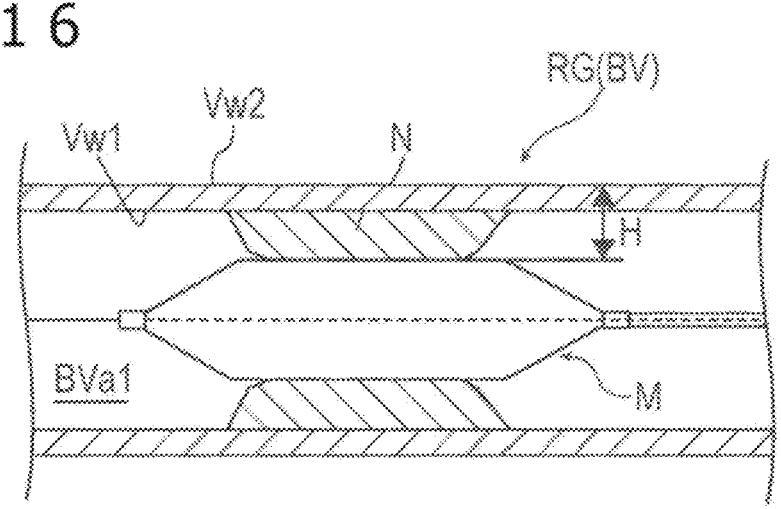

ROUTE SELECTION ASSISTANCE SYSTEM, RECORDING MEDIUM ON WHICH ROUTE SELECTION ASSISTANCE PROGRAM IS RECORDED, ROUTE SELECTION ASSISTANCE METHOD, AND DIAGNOSIS METHOD

CROSS-REFERENCES TO RELATED APPLICATIONS

This application is a continuation of International Application No. PCT/JP2018/020531 filed on May 29, 2018, which claims priority to Japanese Application No. 2017-110379 filed on Jun. 2, 2017, the entire content of both of which is incorporated herein by reference.

FIELD OF THE DISCLOSURE

The present disclosure relates to a route selection assistance system assisting in selecting a route of a living body lumen for delivering a medical instrument to a site within a living body via the living body lumen, a recording medium on which a route selection assistance program is recorded, a route selection assistance method, and a diagnosis method.

BACKGROUND

Procedures are known which perform treatment (expansion of a constriction of a blood vessel), examination (imaging of an inside region of a blood vessel), by delivering a medical instrument to a site within a living body via the blood vessel (living body lumen) (see JP 2014-230710A, for example).

The medical instrument can be introduced from the outside of the living body via a site as an access point to the blood vessel (which site will hereinafter be an introduction site) into the blood vessel, and is delivered to a target site as a target of the procedure via a plurality of sites of the blood vessel. For example, in a case where a blood vessel of a lower limb is treated by using transradial intervention (TRI), the medical instrument can be introduced from a radial artery into the blood vessel, and delivered to the target site of the lower limb via an aortic arch, an aorta (descending aorta), and an iliac artery. TRI is a procedure that has recently been performed because of a relatively small burden on a patient as compared with transfemoral intervention (TFI) that introduces a medical instrument from a femoral artery.

There are a plurality of routes of blood vessels leading from the introduction site to the target site depending on the introduction site. An operator such as a doctor needs to select an appropriate route in consideration of the relative ease of delivery of a medical instrument at a time of delivery of the medical instrument, a relative burden on the patient, and the like. The relative ease of delivery of the medical instrument changes according to the magnitude of bending and curvature of sites of the blood vessel constituting a route, for example.

However, the magnitude of bending and curvature of sites of the blood vessel differs for each target patient. Before starting the above-described procedure, the operator can check the magnitude of bending and curvature of sites of the blood vessel by visually recognizing an image of the inside of the living body of the target patient, and selecting an appropriate blood vessel route, which can depend on the experience of the operator, which can be a relatively great burden on the operator.

In a case of performing treatment of the blood vessel of a lower limb using TRI, for example, the number of sites of the blood vessel to be passed is increased as compared with TFI.

In TFI, when a retrograde puncture is performed from an ipsilateral femoral artery, the femoral artery and an iliac artery as a target of treatment are reached, and when a crossover approach is performed from a contralateral femoral artery, an aortic bifurcation is passed from the femoral artery and an iliac artery, and an iliac artery or a femoral artery on an opposite side is reached.

On the other hand, in performing treatment of a blood vessel of a lower limb from TRI, at a time of insertion from a right radial artery, an aortic arch is generally passed from the right radial artery, a right brachial artery, a right axillary artery, a right subclavian artery, and a brachiocephalic artery. At a time of insertion from a left radial artery, the aortic arch is generally passed from the left radial artery, a left brachial artery, a left axillary artery, the right subclavian artery, and the brachiocephalic artery. After the aortic arch is reached, a thoracic aorta and an abdominal aorta (descending aorta) are passed, and the aortic bifurcation is reached.

Further reached to treat a lower limb artery are left or right one of common iliac arteries, external iliac arteries, internal iliac arteries, common femoral arteries, superficial femoral arteries, and deep femoral arteries, and further, as required, popliteal arteries, anterior tibial arteries, posterior tibial arteries, peroneal arteries, dorsalis pedis arteries, plantar arteries, and other arteries of the lower limbs, peripheral blood vessels connected thereto, and the like.

The magnitude of bending and curvature of sites of these blood vessels or the like differs greatly for each target patient depending on age, a medical history, and the like. Further, in TRI, the blood vessel of the introduction site is thin as compared with a brachial artery puncture and TFI, and the radial arteries are muscular arteries and thus tend to cause spasm (angiospasm). Therefore, in the case of performing treatment of the blood vessel of a lower limb or the like by using TRI, there is a particularly great burden of the work of selecting the route of an appropriate blood vessel as described above.

SUMMARY

A route selection assistance system is disclosed, which helps enable relatively easy selection of a route of a living body lumen for delivering a medical instrument to a site within a living body via the living body lumen, a recording medium on which a route selection assistance program is recorded, a route selection assistance method, and a diagnosis method.

A route selection assistance system according to the present disclosure is a route selection assistance system for assisting in selecting a route of a living body lumen for delivering a medical instrument to a site within a living body via the living body lumen, the route selection assistance system including: a receiving section configured to receive an input of site information specifying a target site within the living body as a target of delivering the medical instrument; an image obtaining section configured to obtain image information on an inside of the living body of a target patient as the target of delivering the medical instrument; a route extracting section configured to extract a plurality of routes of the living body lumen, the plurality of routes allowing the medical instrument to be delivered to the target site, on a basis of the image information obtained by the image obtaining section; a ranking assigning section including a route score calculating section configured to calculate route scores determined according to ease of delivery of the medical instrument at a time of delivery of the medical instrument via the routes and a patient score calculating section configured to calculate patient scores determined according to magnitude of a burden imposed on the target patient, the ranking assigning section assigning rankings to the plurality of routes extracted by the route extracting section by using the route scores and the patient scores; and an output section configured to output the plurality of routes extracted by the route extracting section and the rankings assigned by the ranking assigning section, the image information including an imaging image of the living body lumen, and the route score calculating section calculating the route scores using the imaging image.

A computer readable recording medium according to the present disclosure is a computer readable recording medium on which a route selection assistance program assisting in selecting a route of a living body lumen for delivering a medical instrument to a site within a living body via the living body lumen is recorded, the route selection assistance program making a computer perform: receiving an input of site information specifying a target site within the living body as a target of delivering the medical instrument; obtaining image information on an inside of the living body of a target patient as a target of delivering the medical instrument; extracting a plurality of routes of the living body lumen, the plurality of routes allowing the medical instrument to be delivered to the target site, on a basis of the obtained image information; calculating route scores determined according to ease of delivery of the medical instrument at a time of delivery of the medical instrument via the routes, calculating patient scores determined according to magnitude of a burden imposed on the target patient, and assigning rankings to the extracted plurality of routes by using the calculated route scores and the calculated patient scores; outputting the extracted plurality of routes and the assigned rankings; and the image information including an imaging image of the living body lumen, calculating the route scores by using the imaging image of the living body lumen when the route scores are calculated.

A route selection assistance method according to the present disclosure is a method of assisting in selecting a route of a living body lumen for delivering a medical instrument to a site within a living body via the living body lumen, the method including: receiving an input of site information specifying a target site within the living body as a target of delivering the medical instrument; obtaining image information on an inside of the living body of a target patient as the target of delivering the medical instrument; extracting a plurality of routes of the living body lumen, the plurality of routes allowing the medical instrument to be delivered to the target site, on a basis of the obtained image information; assigning rankings to the extracted plurality of routes by using route scores determined according to ease of delivery of the medical instrument at a time of delivery of the medical instrument via the routes and patient scores determined according to magnitude of a burden imposed on the target patient; and outputting the extracted plurality of routes and the assigned rankings. The image information includes an imaging image of the living body lumen, and the route scores are calculated by using the imaging image of the living body lumen when the route scores are calculated.

A diagnosis method according to the present disclosure is a method for diagnosing a route of a living body lumen for delivering a medical instrument to a site within a living body via the living body lumen, the method including: receiving an input of site information specifying a target site within the living body as a target of delivering the medical instrument; obtaining image information on an inside of the living body of a target patient as the target of delivering the medical instrument; extracting a plurality of routes of the living body lumen, the plurality of routes allowing the medical instrument to be delivered to the target site, on a basis of the obtained image information; assigning rankings to the extracted plurality of routes by using route scores determined according to ease of delivery of the medical instrument at a time of delivery of the medical instrument via the routes and patient scores determined according to magnitude of a burden imposed on the target patient; and diagnosing the route from the extracted plurality of routes and the assigned rankings. The image information includes an imaging image of the living body lumen, and the route scores are calculated by using the imaging image of the living body lumen when the route scores are calculated.

According to the route selection assistance system, the recording medium on which the route selection assistance program is recorded, the route selection assistance method, and the diagnosis method in accordance with the present disclosure, the ranking assigning section assigns rankings to the plurality of routes extracted by the route extracting section by using route scores determined according to relative ease of delivery of the medical instrument at a time of delivery of the medical instrument and patient scores determined according to the magnitude of a relative burden imposed on the target patient. The output section then outputs the plurality of routes extracted by the route extracting section and the rankings assigned by the ranking assigning section. An operator, for example, a doctor can thereby select an appropriate route rather easily from among the plurality of routes of living body lumens through which the medical instrument can be delivered to the target site as a target of a procedure in consideration of the relative ease of delivery of the medical instrument at a time of delivery of the medical instrument and the magnitude of a relative burden imposed on the target patient. Hence, according to the route selection assistance system, the recording medium on which the route selection assistance program is recorded, the route selection assistance method, and the diagnosis method in accordance with the present disclosure, it is possible to rather easily select a route of a living body lumen for delivering the medical instrument to a site within the living body via the living body lumen.

BRIEF DESCRIPTION OF THE DRAWINGS

FIG. 3 is a schematic diagram depicting a screen of a display of the route selection assistance system according to the first embodiment.

FIG. 4 is a diagram schematically depicting a data structure of an introduction site list.

FIG. 12 is a schematic diagram depicting a screen of a display of the route selection assistance system according to the second embodiment.

FIG. 13A is a diagram schematically depicting a data structure of a medical instrument list.

FIG. 13B is a diagram schematically depicting a data structure of a device list.

FIG. 13C is a diagram schematically depicting a data structure of a device information list.

FIG. 14 is a schematic diagram depicting the screen of the display of the route selection assistance system according to the second embodiment.

FIG. 15 is a diagram schematically showing a data structure of a device information list used in a route selection assistance system according to a first modification of the second embodiment.

FIG. 16 is a diagram of assistance in explaining functions of a route selection assistance system according to a second modification of the second embodiment, and is a diagram schematically showing a lesion site.

DETAILED DESCRIPTION

Figure 1:
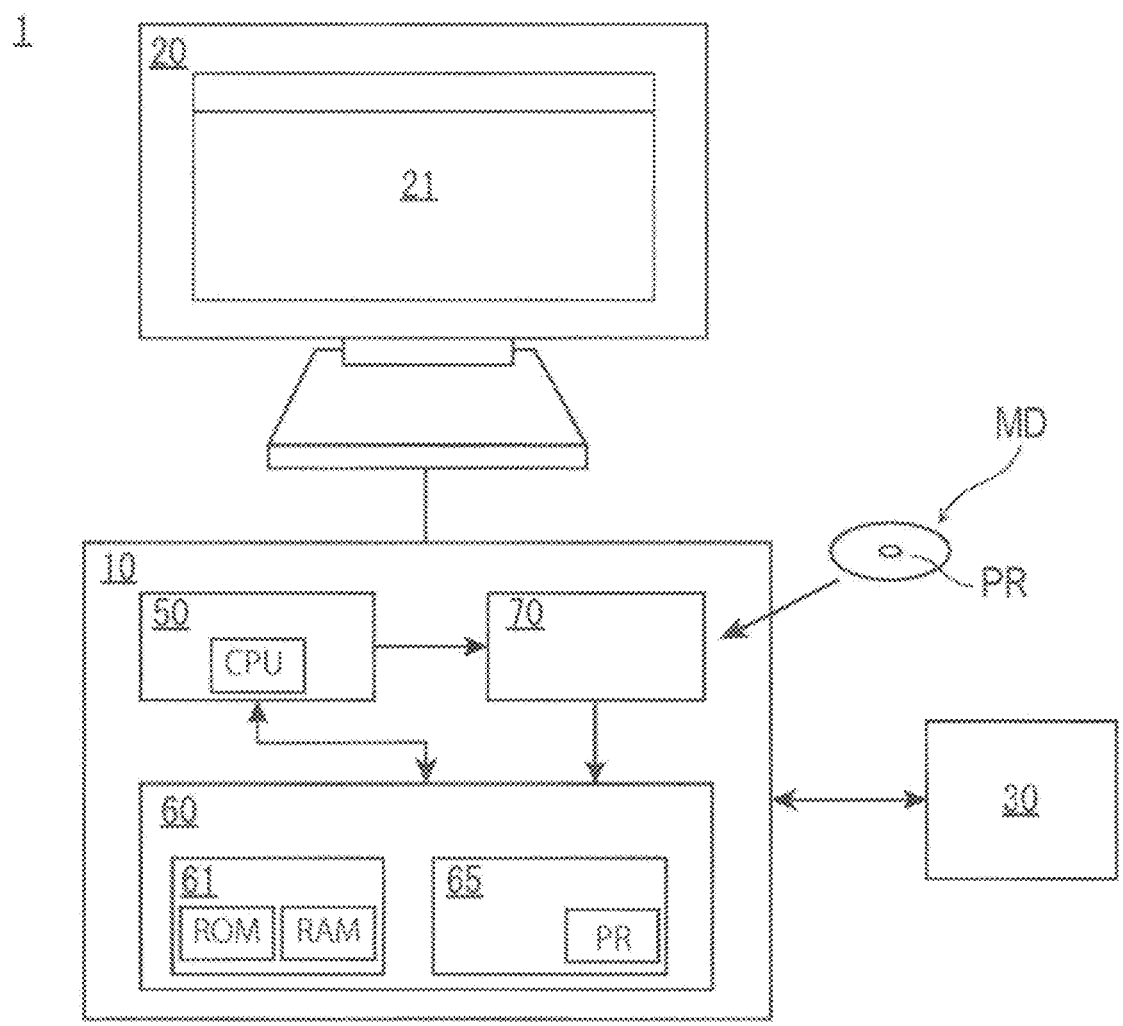
FIG. 1 is a schematic diagram depicting a device configuration of a route selection assistance system according to a first embodiment.

Embodiments of the present disclosure will hereinafter be described with reference to the drawings. It is to be noted that the dimensional ratios in the drawings are exaggerated for the convenience of description, and may be different from actual ratios.

First Embodiment

A route selection assistance system 1 according to the present embodiment is a route selection assistance system that assists in selecting a route RT of a blood vessel BV (corresponding to a living body lumen) for delivering a medical instrument to a site within a living body BD via the blood vessel BV.

Figure 2:
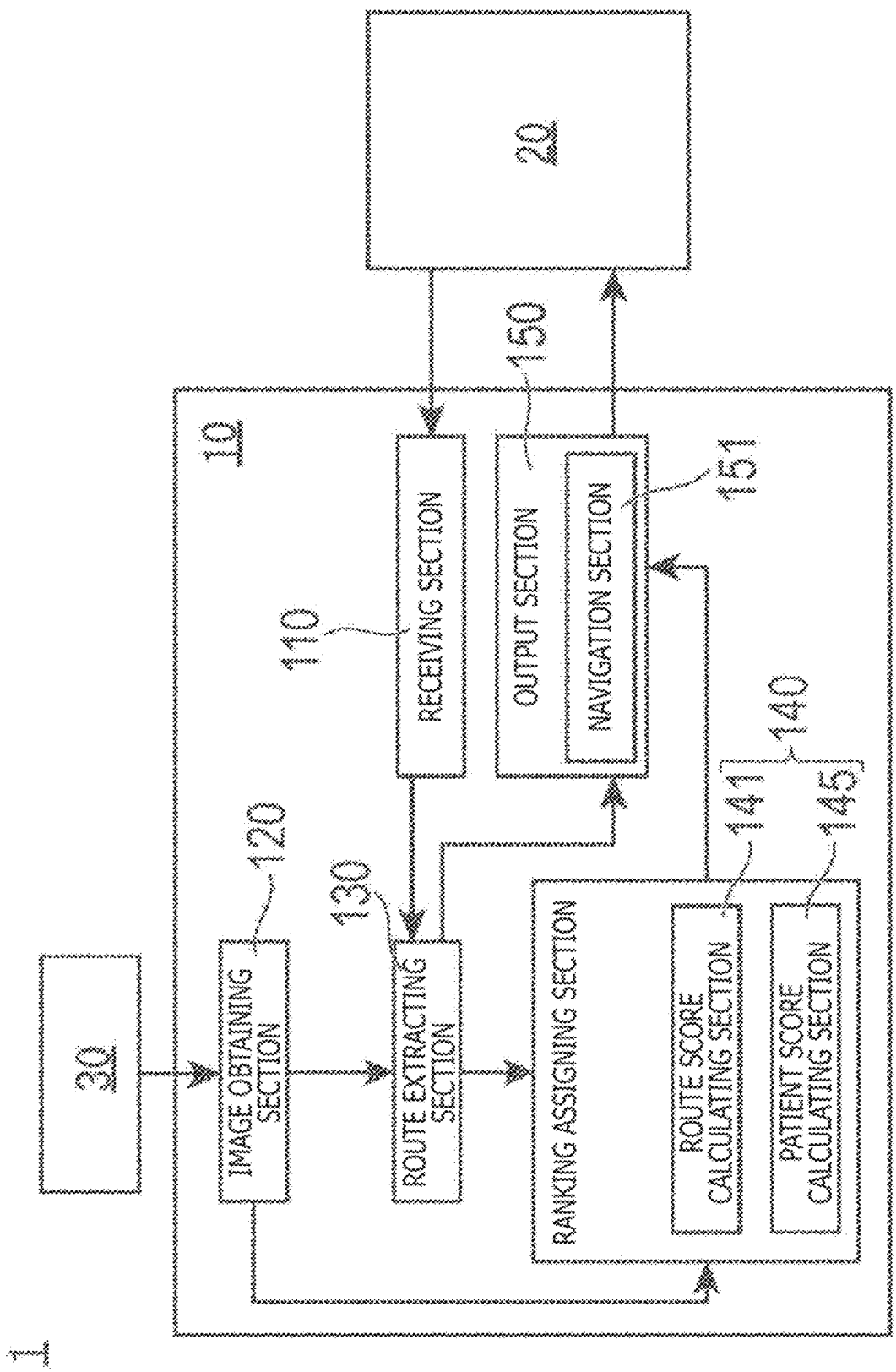
FIG. 2 is a block diagram depicting a functional configuration of the route selection assistance system according to the first embodiment.

FIG. 1 is a schematic diagram of assistance in explaining a device configuration of the route selection assistance system 1. FIG. 2 is a block diagram of assistance in explaining a functional configuration of the route selection assistance system 1. FIGS. 3 to 9 are diagrams of assistance in explaining various functions of the route selection assistance system 1.

A device configuration of the route selection assistance system 1 will be described.

Referring to FIG. 1, the route selection assistance system 1 includes a computer main unit 10 and a display 20. The computer main unit 10 is connected to an external server 30.

The computer main unit 10 includes an arithmetic unit 50, a storage device 60, and a reading device 70.

The arithmetic unit 50 performs operation on the basis of a program and data stored in the storage device 60. The arithmetic unit 50 can be any suitable central processing unit (CPU) (i.e., processor).

The storage device 60 includes a memory circuit 61 and a hard disk drive 65. The memory circuit 61 can include a read only memory (ROM) and a random access memory (RAM).

In accordance with an exemplary embodiment, the storage device 60 stores a basic program such as an operating system (OS), a route selection assistance program PR making the arithmetic unit 50 perform functions of the route selection assistance system 1, and data processed by the route selection assistance program PR.

The reading device 70 reads information recorded on a computer readable recording medium MD. The computer readable recording medium MD can be for example an optical disk such as a compact disk (CD)-ROM, or a digital video disk (DVD)-ROM, a universal serial bus (USB) memory, or a secure digital (SD) memory card. The reading device 70 can be, for example, a CD-ROM drive, or a DVD-ROM drive.

In accordance with an exemplary embodiment, the route selection assistance program PR is provided in a state of being recorded on the computer readable recording medium MD. The reading device 70 reads the route selection assistance program PR recorded on the computer readable recording medium MD. The route selection assistance program PR read by the reading device 70 is stored on the hard disk drive 65.

The display 20 is connected to the computer main unit 10. The display 20 transmits and receives information to and from the computer main unit 10.

The display 20 can include a screen 21 that inputs and outputs information. The display 20 outputs information received from the computer main unit 10 on the screen 21. The display 20 transmits information input via the screen 21 to the computer main unit 10. The display 20 can be any suitable touch panel display.

The computer main unit 10 transmits and receives information to and from the external server 30.

The computer main unit 10 and the external server 30 are connected to each other via a network. The kind (i.e., type) of the network is not particularly limited. For example, the network may be a network of a wired system using a local area network (LAN) cable or the like, or may be a network of a radio system using wireless fidelity (Wi-Fi) or the like.

A functional configuration of the route selection assistance system 1 will next be described.

Referring to FIG. 2, the route selection assistance system 1 includes a receiving section 110, an image obtaining section 120, a route extracting section 130, a ranking assigning section 140, and an output section 150.

Operation related to processing of the receiving section 110, the image obtaining section 120, the route extracting section 130, the ranking assigning section 140, and the output section 150 is performed by the arithmetic unit 50. Data processed by the receiving section 110, the image obtaining section 120, the route extracting section 130, the ranking assigning section 140, and the output section 150 is stored in the storage device 60.

Referring to FIG. 3, the receiving section 110 receives an input of site information specifying a target site RG as a target of a procedure to be performed by delivering a medical instrument. The receiving section 110 receives the input of the site information via the display 20.

Though not particularly limited, the target site RG can be, for example, a left and a right common iliac artery, external iliac arteries, internal iliac arteries, common femoral arteries, superficial femoral arteries, deep femoral arteries, popliteal arteries, anterior tibial arteries, posterior tibial arteries, peroneal arteries, dorsalis pedis arteries, plantar arteries, and other arteries of lower limbs, or collateral circulations, peripheral blood vessels connected to arteries as described above.

The image obtaining section 120 obtains image information DT1 within the living body BD of a target patient as a target of a procedure to be performed by delivering a medical instrument.

Figure 6A:
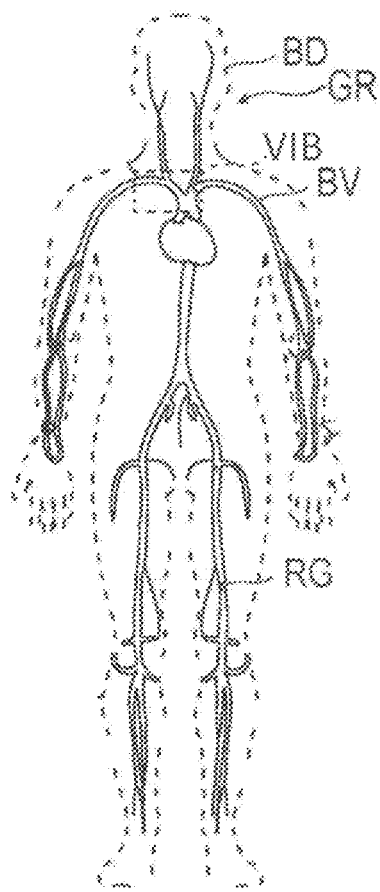
FIG. 6A is a diagram schematically depicting an image of a living body of a target patient.
Figures 8A, 8B:
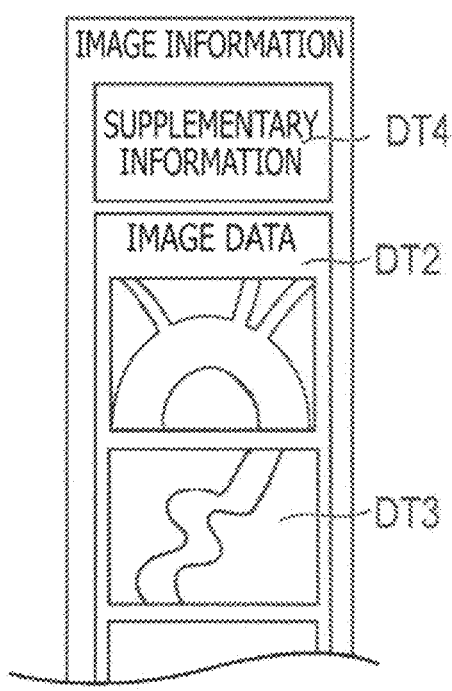
FIG. 8A is a diagram schematically depicting a data structure of image information.
FIG. 8B is a diagram schematically depicting a data structure of supplementary information.

Referring to FIG. 6A and FIG. 8A, the image information DT1 includes image data DT2 within the living body BD of the target patient which living body is photographed by a medical image photographing device. In accordance with an exemplary embodiment, the image data DT2 of the living body BD is three-dimensional image data.

Though not particularly limited, the data format of the image information DT1 can be, for example, digital imaging and communication in medicine (DICOM).

In accordance with an exemplary embodiment, the image information DT1 can be stored in the external server 30. The image obtaining section 120 obtains the image information DT1 from the external server 30 via the network.

In accordance with an exemplary embodiment, the route extracting section 130 extracts a plurality of routes RT of blood vessels BV through which a medical instrument can be delivered to the target site RG on the basis of the image information DT1 obtained by the image obtaining section 120. Though not particularly limited, the number of routes RT of blood vessels BV extracted by the route extracting section 130 can be, for example, 6.

For each candidate for a site as an access point at a time of introduction of a medical instrument from the outside of the living body BD to a blood vessel BV (which site will hereinafter be an introduction site RS), the route extracting section 130 extracts the route RT of the blood vessel BV leading from the target site RG to the introduction site RS.

Though not particularly limited, candidates for the introduction site RS can be, for example, a right radial artery, a right brachial artery, a right subclavian artery, a right carotid artery, a right femoral artery, a left radial artery, a left brachial artery, a left subclavian artery, a left carotid artery, and a left femoral artery. Candidates for the introduction site RS may also be, for example, a popliteal artery, an anterior tibial artery, a posterior tibial artery, a peroneal artery, a dorsalis pedis artery, a plantar artery, and other blood vessels of an ankle.

In addition, the radial artery may be a distal radial artery or a radial artery located in a snuff box.

Referring to FIG. 4, the route extracting section 130 extracts the route RT of the blood vessel BV leading from the target site RG to the introduction site RS by using an introduction site list LS1 in which candidates for the introduction site RS are recorded. The introduction site list LS1 can be, for example, stored in the external server 30. The route extracting section 130 obtains the introduction site list LS1 from the external server 30 via the network. Details of processing in the route extracting section 130 will be described later.

Referring to FIG. 2, the ranking assigning section 140 includes a route score calculating section 141 that calculates a route score SR determined according to ease of delivery of a medical instrument and a patient score calculating section 145 that calculates a patient score SP determined according to the magnitude (i.e., size or extent) of a relative burden imposed on the target patient.

The ranking assigning section 140 assigns rankings to the plurality of routes RT extracted by the route extracting section 130 by using the route score SR calculated by the route score calculating section 141 and the patient score SP calculated by the patient score calculating section 145.

The ranking assigning section 140 assigns rankings to the plurality of routes RT extracted by the route extracting section 130 in increasing order of a product SR×SP of the route score SR calculated by the route score calculating section 141 and the patient score SP calculated by the patient score calculating section 145.

In accordance with an exemplary embodiment, the route score calculating section 141 calculates the route score SR on the basis of a length L of the route RT and a bending degree P of the route RT. The route score calculating section 141 calculates, as the route score SR, a product L×P of the length L of the route RT and the bending degree P of the route RT.

Figure 5:
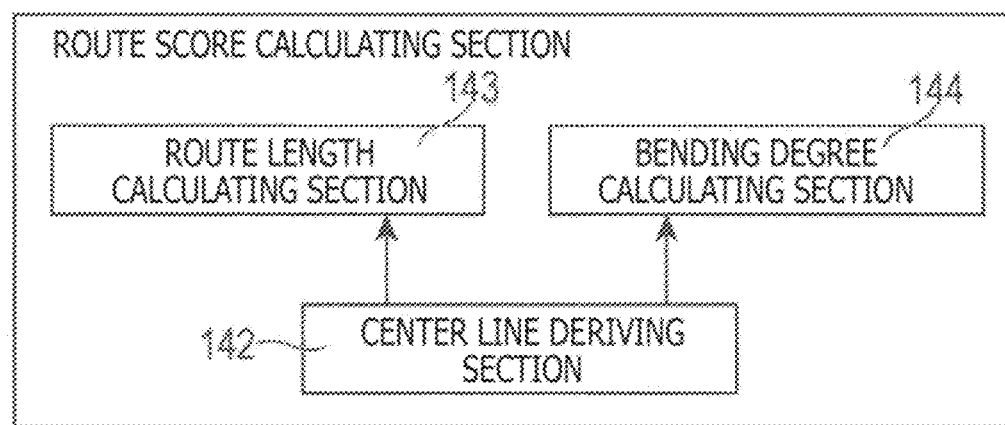
FIG. 5 is a block diagram depicting a functional configuration of a route score calculating section of the route selection assistance system according to the first embodiment.

Referring to FIG. 5, the route score calculating section 141 includes a center line deriving section 142 that calculates a center line CL of the route RT extracted by the route extracting section 130, a route length calculating section 143 that calculates the length L of the route RT, and a bending degree calculating section 144 that calculates the bending degree P of the route RT.

Figure 6B:
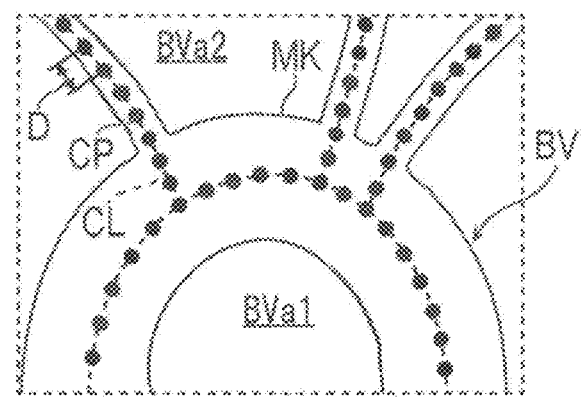
FIG. 6B is an enlarged view of a region enclosed by a broken line part VIB in FIG. 6A.

Referring to FIG. 6B, image data DT2 can include an imaging image of the blood vessel BV. The imaging image of the blood vessel BV is an image photographed with the blood vessel BV as a target. The imaging image of the blood vessel BV can be, for example, an image of an inside region BVa1 of the blood vessel BV, the image being obtained by using an intravascular ultrasound diagnosis method (IVUS: intra vascular ultra sound) or an optical coherence tomography diagnosis method (OCT: optical coherence tomography), an angiographic X-ray computed tomography (CT) image, a non-contrast magnetic resonance angiography (MRA) image, or the like. The imaging image of the blood vessel BV may be an angiographic image for which a contrast medium can be used. In addition, the imaging image of the blood vessel BV may be a cine image.

In accordance with an exemplary embodiment, the center line deriving section 142 calculates centers CP of the blood vessel BV on the basis of the imaging image of the blood vessel BV, and derives a center line CL of the blood vessel BV by connecting the centers CP of the blood vessel BV leading from the target site RG to the introduction site RS. In accordance with an exemplary embodiment, a "center CP of the blood vessel BV" refers to a center of a region enclosed by a blood vessel wall in a cross section of the blood vessel BV.

In accordance with an exemplary, the center line deriving section 142 discretely calculates the centers CP of the blood vessel BV at predetermined intervals D, and derives the center line CL by interpolation between the calculated centers CP. The intervals D may be a fixed value, or may be a variable value. The size of the intervals D is not particularly limited. A method of the interpolation between the centers CP is not particularly limited, but may be linear interpolation or may be polynomial interpolation or spline interpolation.

In accordance with an exemplary embodiment, the route length calculating section 143 calculates a length of the center line CL calculated by the center line deriving section 142 as a length L of the route RT. The route length calculating section 143 calculates a sum of distances between the centers CP discretely calculated by the center line deriving section 142 as the length of the center line CL.

In accordance with an exemplary embodiment, the bending degree calculating section 144 calculates a bending degree of the center line CL derived by the center line deriving section 142 as a bending degree P of the route RT. Incidentally, the "bending degree" is a sum total of the magnitude of bendings or curves calculated for each part bent or curved in the center line CL of the blood vessel BV. The "magnitude of bendings or curves" can be expressed by using curvature. The "bending degree" is not limited to a continuous numerical value, but may be a discrete value such as "large," "medium," or "small."

Figure 6C:
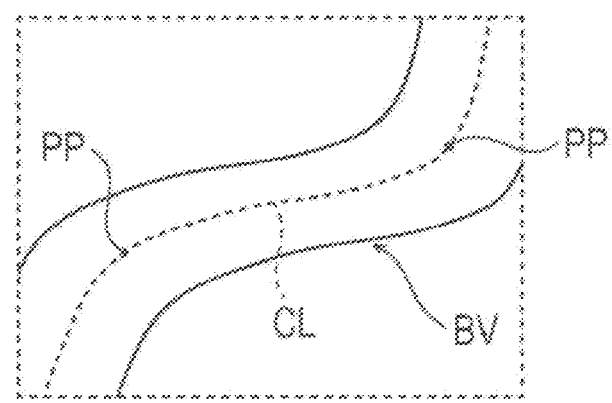
FIG. 6C is a schematic diagram in explaining a method of calculating the bending degree of a route in the route selection assistance system according to the first embodiment.

Referring to FIG. 6C, for each vertex PP of the center line CL of the blood vessel BV, the bending degree calculating section 144 calculates a curvature of the center line CL at the vertex PP, and calculates a sum of curvatures calculated for respective vertices PP as the bending degree P. In accordance with an exemplary embodiment, the bending degree calculating section 144 may set a maximum value of the curvatures calculated for the respective vertices PP as the bending degree P. In accordance with an exemplary embodiment, a "vertex PP of the center line CL" is a point at which the curvature is at a maximum or a minimum in the center line CL.

The patient score calculating section 145 calculates the patient score SP by using an invasion degree (i.e., invasion level) of the route RT extracted by the route extracting section 130.

The invasion degree can be, for example, determined according to an amount of bleeding, for example, at a time of introduction of a medical instrument into the blood vessel BV via the introduction site RS, a time from an end of the procedure to the stopping of the bleeding, or the like. The invasion degree of the route RT whose introduction site RS can be a radial artery, for example, is smaller than the invasion degree of the route RT whose introduction site RS is, for example, a femoral artery.

Referring to FIG. 4, recorded in the introduction site list LS1 for each candidate for the introduction site RS is the invasion degree at a time of introduction of a medical instrument into the blood vessel BV via the corresponding introduction site RS.

The patient score calculating section 145 calculates the invasion degree of the route RT extracted by the route extracting section 130 by using the invasion degree recorded in the introduction site list LS1. The patient score calculating section 145 obtains the introduction site list LS1 from the external server 30 via the network.

Figure 7A:
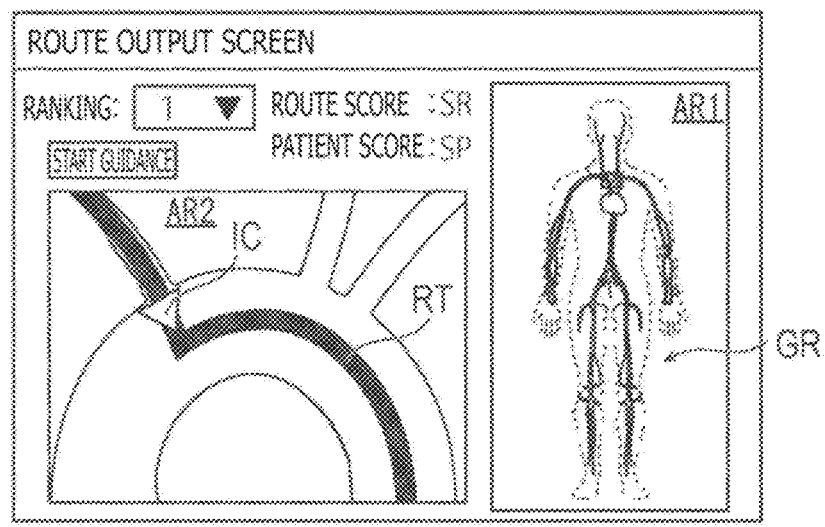
FIG. 7A is a schematic diagram depicting the screen of the display of the route selection assistance system according to the first embodiment.
Figure 7B:
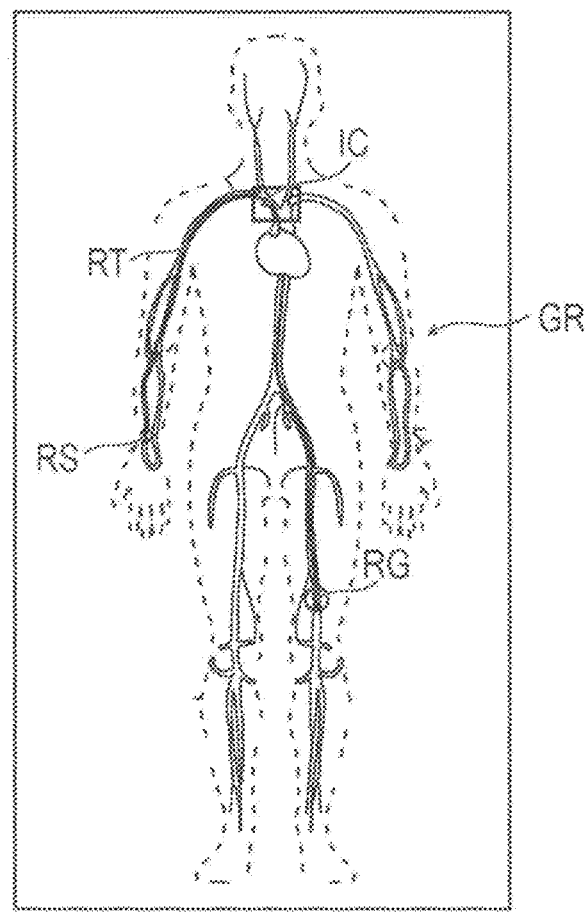
FIG. 7B is a schematic diagram depicting a route display region of the screen.

Referring to FIG. 7A and FIG. 7B, the output section 150 outputs, to the display 20, the plurality of routes RT extracted by the route extracting section 130, the rankings assigned by the ranking assigning section 140, the route score SR, and the patient score SP. The output section 150 outputs the plurality of routes RT extracted by the route extracting section 130 on the display 20 together with an image GR of the living body BD of the target patient.

In accordance with an exemplary embodiment, the output section 150 displays the plurality of routes RT extracted by the route extracting section 130 in a route display region AR1 of the display 20. The output section 150 displays an enlarged image of the plurality of routes RT extracted by the route extracting section 130 in a detailed display region AR2.

In accordance with an exemplary embodiment, the output section 150 may display information identifying a site having a largest bending degree P (which site will hereinafter be a maximum bending site) in which site a device causes a kink or the like and it is thus expected to be difficult for the device to pass (which information is for example the name of the site of the blood vessel BV) and a numerical value indicating a degree of bending such as a curvature, an angle (angle θ to be described later with reference to FIG. 22 or the like), or the like at the site. The output section 150 can perform processing of displaying these on the basis of the bending degree P calculated by the bending degree calculating section 144.

In addition, the output section 150 may display not only the maximum bending site but also information identifying other sites and degrees of bending in order of the magnitude of the bending degree P.

The receiving section 110 receives a selection of a route RT output to the display 20 by the output section 150. In response to the selection of the route RT which selection is received by the receiving section 110, the output section 150 displays, on the display 20, one route RT of the plurality of routes RT extracted by the route extracting section 130, a ranking corresponding to the one route RT, a route score SR, and a patient score SP.

Referring to FIG. 2, the output section 150 can include a navigation section 151 that guides the medical instrument through the route RT extracted by the route extracting section 130.

In accordance with an exemplary embodiment, the receiving section 110 receives an operation for starting the guidance through the route RT extracted by the route extracting section 130. In accordance with an exemplary embodiment, when the receiving section 110 receives the operation for starting the guidance through the route RT, the navigation section 151 starts guiding through the route RT.

The navigation section 151 estimates the position of an end of a medical instrument to be delivered to a site within a living body BD via the blood vessel BV, and displays an icon IC indicating the estimated position of the end of the medical instrument on the route RT.

The navigation section 151 displays the route RT extracted by the route extracting section 130 and the icon IC indicating the position of the end of the medical instrument on the display 20 together with the image data DT2 of the blood vessel BV.

A method of estimating the position of the end of the medical instrument is not particularly limited. For example, the estimation may be performed on the basis of an average moving speed of the medical instrument in the blood vessel BV, or the estimation may be performed by actually measuring the length of the medical instrument introduced into the blood vessel BV on the base end side of the medical instrument. In addition, in a case where a contrast marker is provided to an end portion of the medical instrument, a position estimating section may correct the estimated position of the end of the medical instrument by imaging the contrast marker.

Processing in the route extracting section 130 will next be explained in detail.

Referring to FIG. 8A and FIG. 8B, the image information DT1 includes divided image data DT3 obtained by dividing the image data DT2 into a plurality of pieces and supplementary information DT4 recorded as information about the divided image data DT3.

The divided image data DT3 is data generated by dividing the image data DT2 according to sites of the blood vessel BV. For example, the divided image data DT3 is data generated by dividing the image data DT2 for each site of a right subclavian artery, a brachiocephalic artery, an aortic arch, a thoracic aorta, an abdominal aorta, a left common iliac artery, a left external iliac artery, a left femoral artery, or the like. Divided images are identified by unique identifiers (hereinafter IDs).

Recorded as the supplementary information DT4 for each piece of divided image data DT3 are site information specifying a site of the blood vessel BV included in the corresponding divided image data DT3 and link information bidirectionally linking adjacent pieces of divided image data DT3 to each other.

Figure 9:
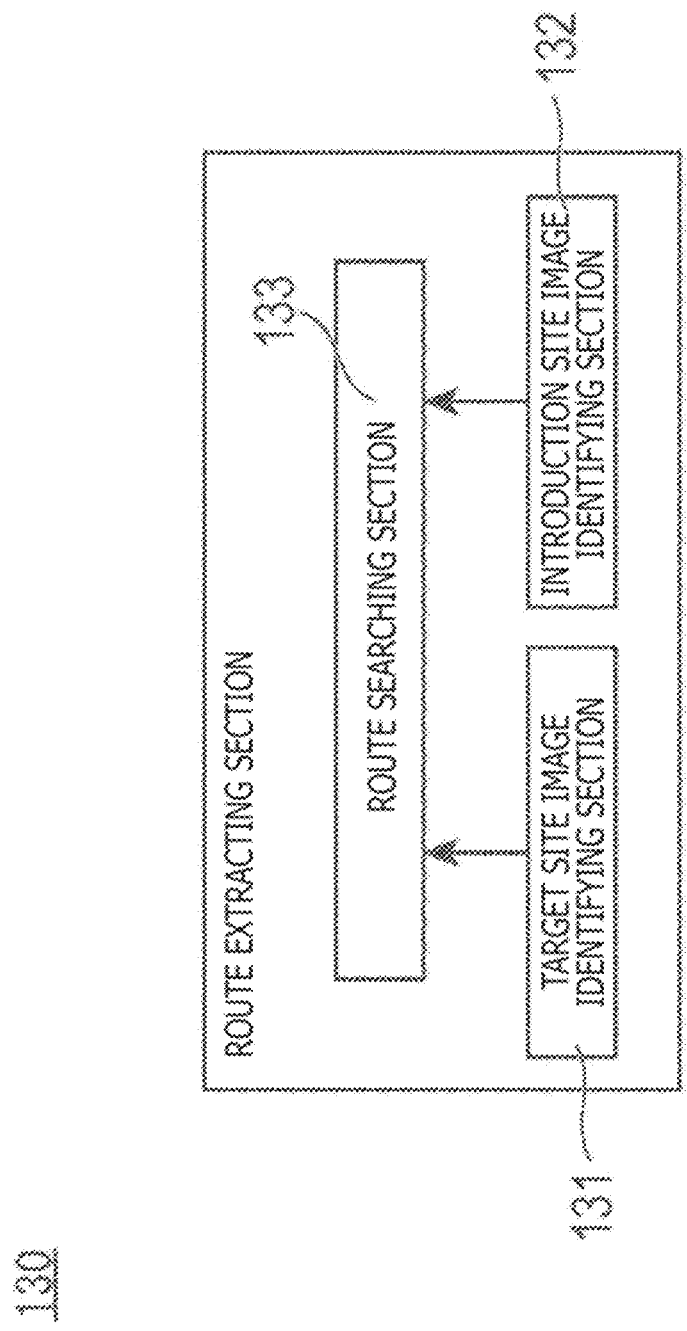
FIG. 9 is a block diagram depicting a functional configuration of a route extracting section of the route selection assistance system according to the first embodiment.

Referring to FIG. 9, the route extracting section 130 includes: a target site image specifying section 131 that specifies the ID of a piece of divided image data DT3 including the target site RG from among the plurality of pieces of divided image data DT3 included in the image information DT1; an introduction site image specifying section 132 that specifies the ID of a piece of divided image data DT3 including a candidate for the introduction site RS from among the plurality of pieces of divided image data DT3 included in the image information DT1; and a route searching section 133 that searches for the route RT of the blood vessel BV leading from the target site RG to the introduction site RS.

In accordance with an exemplary embodiment, the target site image specifying section 131 specifies the ID of the piece of divided image data DT3 including the target site RG by using the site information received by the receiving section 110 and the site information included in the supplementary information DT4.

The introduction site image specifying section 132 specifies the ID of a piece of divided image data DT3, for example, including a candidate for the introduction site RS by using the introduction site list LS1 and the site information included in the supplementary information DT4.

The route searching section 133 searches for the route RT of the blood vessel BV leading from the target site RG to the introduction site RS by using the ID of a divided image specified by the target site image specifying section 131, the ID of a divided image specified by the introduction site image specifying section 132, and the link information included in the supplementary information DT4.

Description will next be made of a method of assisting in selecting the route RT of the living body lumen for delivering a medical instrument to a site within a living body via the living body lumen (which method will hereinafter be a route selection assistance method).

Figure 10:
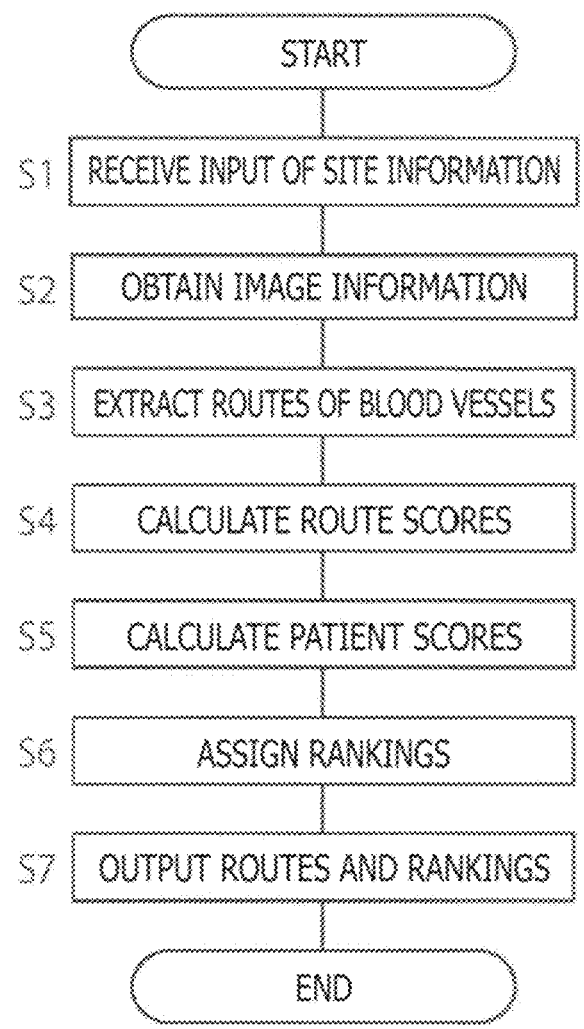
FIG. 10 is a flowchart of assistance in explaining a route selection assistance method according to the first embodiment.

Referring to FIG. 10, the route selection assistance method includes: step S1 of receiving an input of site information; step S2 of obtaining the image information DT1; step S3 of extracting the routes RT of blood vessels BV (corresponding to the living body lumen); step S4 of calculating route scores SR; step S5 of calculating patient scores SP; step S6 of assigning rankings to the extracted routes RT; and step S7 of outputting the extracted routes RT and the rankings.

Step S1 of receiving an input of site information receives the input of the site information specifying the target site RG as a target of a procedure performed by delivering a medical instrument. In accordance with an exemplary embodiment, step S1 of receiving the input of the site information is performed by the receiving section 110.

Step S2 of obtaining the image information DT1 obtains the image information DT1 of the living body BD of the target patient as a target of a procedure performed by delivering a medical instrument. In accordance with an exemplary embodiment, step S2 of obtaining the image information DT1 is performed by the image obtaining section 120.

Step S3 of extracting the routes RT of blood vessels BV extracts a plurality of routes RT of living body lumens through which a medical instrument can be delivered to the target site RG on the basis of the obtained image information DT1. In accordance with an exemplary embodiment, step S3 of extracting the routes RT of the blood vessels BV is performed by the route extracting section 130.

Step S4 of calculating route scores SR calculates the route scores SR determined according to ease of delivery of a medical instrument at a time of delivery of the medical instrument via the routes RT. In accordance with an exemplary embodiment, step S4 of calculating the route scores SR is performed by the route score calculating section 141.

Step S5 of calculating patient scores SP calculates the patient scores SP determined according to the magnitude of a relative burden imposed on the target patient. In accordance with an exemplary embodiment, step S5 of calculating the patient scores SP is performed by the patient score calculating section 145.

Step S6 of assigning rankings assigns rankings to the plurality of extracted routes RT on the basis of the calculated route scores SR and the calculated patient scores SP. In accordance with an exemplary embodiment, step S6 of assigning the rankings is performed by the ranking assigning section 140.

Outputting step S7 outputs, to the display 20, the plurality of routes RT extracted in step S3 of extracting the routes RT of the blood vessels BV, the rankings assigned in step S6 of assigning the rankings, the route scores SR calculated in step S4 of calculating the route scores SR, and the patient scores SP calculated in step S5 of calculating the patient scores SP.

Outputting step S7 outputs, to the display 20, the routes RT, the rankings, the route scores SR, and the patient scores SP in order to assist an operator such as a doctor in selecting the route RT of a blood vessel BV for delivering a medical instrument to the target site RG within the living body BD via the blood vessel BV.

Outputting step S7 outputs the plurality of routes RT extracted by the route extracting section 130 to the display 20 together with the image GR of the living body BD of the target patient.

Outputting step S7 is performed by the output section 150.

Description will next be made of a method of diagnosing the route RT of a blood vessel BV for delivering a medical instrument to a site within the living body BD via the blood vessel BV (corresponding to a living body lumen) (which method will hereinafter be a diagnosis method).

The diagnosis method according to the present embodiment includes a step of diagnosing a route RT from the plurality of routes RT extracted in step S3 of extracting the routes RT of the blood vessels BV and the rankings assigned in step S6 of assigning the rankings in addition to steps S1 to S6 of the route selection assistance method described above.

The step of diagnosing a route RT diagnoses a route RT assigned a high ranking in step S6 of assigning the rankings as a more appropriate route RT as compared with a route RT having a low ranking from a viewpoint of the ease of delivering a medical instrument at a time of delivery of the medical instrument via the route RT and the magnitude of a burden imposed on the target patient.

Description will next be made of an example of usage of the route assistance system according to the present embodiment. In the following, description will be made by taking as an example a case where six sites of a right radial artery, a right brachial artery, a right femoral artery, a left radial artery, a left brachial artery, and a left femoral artery are recorded in the introduction site list LS1 (see FIG. 4). In the following, description will be made by taking as an example a case where a left superficial femoral artery (SFA) is to be treated.

Referring to FIG. 3, by operating the display 20, an operator inputs a "left superficial femoral artery" as site information specifying the target site RG as a target of a procedure performed by delivering a medical instrument.

The image obtaining section 120 obtains the image information DT1 on the inside of the living body BD of the target patient as a target of a procedure performed by delivering a medical instrument from the external server 30 (see FIG. 1) via the network.

In accordance with an exemplary embodiment, the route extracting section 130 extracts six routes RT of blood vessels BV corresponding to six candidates for the introduction site RS, the six candidates being a right radial artery, a right brachial artery, a right femoral artery, a left radial artery, a left brachial artery, and a left femoral artery recorded in the introduction site list LS1 (see FIG. 4).

For each of the six routes RT extracted by the route extracting section 130, the route score calculating section 141 calculates a route score SR on the basis of the length L of the route RT and the bending degree P of the route RT. For each of the six routes RT extracted by the route extracting section 130, the patient score calculating section 145 calculates a patient score SP by using an invasion degree.

In the present usage example, the route score SR is decreased in order of the route RT whose introduction site RS is a right radial artery (left radial artery), the route RT whose introduction site RS is a right brachial artery (left brachial artery), and the route RT whose introduction site RS is a right femoral artery (left femoral artery). In contrast to this, the patient score SP is decreased in order of the route RT whose introduction site RS is the right femoral artery (left femoral artery), the route RT whose introduction site RS is the right brachial artery (left brachial artery), and the route RT whose introduction site RS is the right radial artery (left radial artery).

In the present usage example, the product SR×SP of the route score SR and the patient score SP is decreased in order of the route RT whose introduction site RS is the right femoral artery (left femoral artery), the route RT whose introduction site RS is the right brachial artery (left radial artery), and the route RT whose introduction site RS is the right radial artery (left radial artery).

In accordance with an exemplary embodiment, the ranking assigning section 140 assigns rankings to the plurality of routes RT extracted by the route extracting section 130 in increasing order of the product SR×SP of the route score SR calculated by the route score calculating section 141 and the patient score SP calculated by the patient score calculating section 145.

The output section 150 outputs, to the display 20, the plurality of routes RT extracted by the route extracting section 130, the rankings assigned by the ranking assigning section 140, and the route scores SR and the patient scores SP (see FIG. 7A and FIG. 7B).

The operator such as a doctor refers to the routes RT of the blood vessels BV, the rankings, and the route scores SR and the patient scores SP output to the display 20, and thereby selects an appropriate route RT with consideration given to the ease of delivery of a medical instrument at a time of delivery of the medical instrument and the magnitude of a burden imposed on the target patient.

According to the route selection assistance system 1, the recording medium MD on which the route selection assistance program PR is recorded, the route selection assistance method, and the diagnosis method in accordance with the present embodiment, the ranking assigning section 140 assigns rankings to the plurality of routes RT extracted by the route extracting section 130 by using the route scores SR determined according to the ease of delivery of a medical instrument at a time of delivery of the medical instrument and the patient scores SP determined according to the magnitude of a burden imposed on the target patient. The output section 150 then outputs the plurality of routes RT extracted by the route extracting section 130 and the rankings assigned by the ranking assigning section 140. The operator such as a doctor can thereby select an appropriate route RT easily from among the plurality of routes RT of blood vessels BV through which a medical instrument can be delivered to the target site RG as a target of a procedure in consideration of the ease of delivery of the medical instrument at a time of the delivery of the medical instrument and the magnitude of a burden imposed on the target patient. Hence, according to the route selection assistance system 1, the recording medium MD on which the route selection assistance program PR is recorded, and the route selection assistance method in accordance with the present invention, it is possible to easily select the route RT of a blood vessel BV for delivering a medical instrument to a site within the living body BD via the blood vessel BV. Such an effect is particularly remarkable in a case where the number of sites of the blood vessel BV which sites are to be passed is increased, that is, in a case where the blood vessel BV of a lower limb is treated by using TRI or the like.

In addition, according to the route selection assistance system 1, the recording medium MD on which the route selection assistance program PR is recorded, the route selection assistance method, and the diagnosis method in accordance with the present embodiment, the route score calculating section 141 calculates route scores SR using the imaging image of the blood vessel BV. The route score calculating section 141 can thereby calculate the route scores SR with relatively higher accuracy. Therefore, an operator can rather easily select a more appropriate route RT from among the plurality of routes RT of blood vessels BV through which the medical instrument can be delivered to the target site RG in consideration of the relative ease of delivery of the medical instrument at a time of delivery of the medical instrument.

In addition, according to the route selection assistance system 1, the recording medium MD on which the route selection assistance program PR is recorded, the route selection assistance method, and the diagnosis method in accordance with the present embodiment, the output section 150 includes the navigation section 151 that guides through the route RT extracted by the route extracting section 130. The operator can therefore rather easily deliver the medical instrument to the target site RG via the blood vessel BV according to the guidance through the route RT by the navigation section 151.

First Modification of First Embodiment

In accordance with an exemplary embodiment, the ranking assigning section 140 may adjust the rankings by using patient information about the target patient as a target of delivering the medical instrument.

A route selection assistance system according to a present modification includes a patient information obtaining section (not shown) that obtains the patient information about the target patient as a target of delivering a medical instrument to a site within the living body BD via the blood vessel BV.

The patient information, for example, can include worker identification information distinguishing whether or not the target patient is a worker (for example, business person, sales person, etc.). When the target patient is a worker, the ranking assigning section 140 assigns rankings to the routes RT with priority given to invasion degrees over the lengths L of the routes RT and the bending degrees P of the routes RT. Consequently, the ranking of a route RT having a relatively high invasion degree is adjusted to a low side (i.e., lower priority). Therefore, the operator, for example, a doctor can easily select a route RT having a relatively lower invasion degree than a route RT having a relatively high (or higher) invasion degree when the target patient is a worker.

In accordance with an exemplary embodiment, a "lower invasion degree" means a smaller number of days taken from the execution of a procedure of delivering a medical instrument to the target site RG via the blood vessel BV to discharge of the target patient from the hospital. Therefore, when the target patient is a worker, delivering a medical instrument to the target site RG using a route RT having a relatively low (or lower) invasion degree improves quality of life (QOL) of the target patient.

As described above, when the target patient is a worker, the ranking assigning section 140 adjusts the ranking of a route RT having a high invasion degree to a low side. As a result, when the target patient is a worker, the operator, for example, a doctor can rather easily select a route RT having a relatively lower invasion degree than a route RT having a relatively high (or higher) invasion degree. Therefore, the operator, for example, a doctor can rather easily select a more appropriate route RT according to whether or not the target patient is a worker.

The patient information is not limited to the worker identification information described above, but may be information about the gender, height, weight, age, character, or occupation of the target patient, the state of the blood vessel BV of the target patient, or the like. In accordance with an exemplary embodiment, the information about the state of the blood vessel BV can record presence or absence of calcification and chronic total occlusion (CTO) for each site of the blood vessel BV.

For example, on the basis of the bending degrees P of the routes RT and the information about the age and the state of the blood vessel BV which information is included in the patient information, when the target patient is of a relatively advanced age, the ranking assigning section 140 may give priority to the bending degrees P of the routes RT and the state of the blood vessel BV (presence or absence of calcification and CTO) over the invasion degrees, and adjust the ranking of a route RT imposing a relatively small (or smaller) burden on the blood vessel BV to a relatively high (or higher) side. Thus, when the target patient is of a relatively advanced age, the operator, for example, a doctor can rather easily select a route RT imposing a relatively small (or smaller) burden on the blood vessel BV instead of the invasion degree. Therefore, according to the route selection assistance system in accordance with the present modification, the operator, for example, a doctor can rather easily select an appropriate route RT with consideration given to the burden on the target patient according to the age of the target patient.

According to the route selection assistance system, the recording medium on which the route selection assistance program is recorded, the route selection assistance method, and the diagnosis method in accordance with the present modification, the operator, for example, a doctor can rather easily select a more appropriate route RT according to the target patient.

Second Modification of First Embodiment

In accordance with an exemplary embodiment, the bending degree calculating section 144 may calculate a bending degree P for one or a plurality of selected sites selected in advance on the basis of the magnitude of bendings or curves among sites of the blood vessel BV, and calculate a sum of the calculated bending degrees P as the bending degree P of the route RT, which can reduce an amount of calculation as compared with a case where bending degrees are calculated for all of the sites of the blood vessel BV constituting the route RT extracted by the route extracting section 130. In accordance with an exemplary embodiment, the bending degree calculating section 144 may set a maximum value of the bending degrees P calculated for the respective selected sites as the bending degree P of the route RT.

In accordance with an exemplary embodiment, a selected site can be, for example, a site predicted to have a steep bending or curve or a site predicted to have a significant difference in the magnitude of a bending or a curve for each target patient among the sites of the blood vessel BV constituting the route RT. For example, in a route RT whose introduction site RS is a radial artery and whose target site RG is the blood vessel BV of a lower limb, selected sites can be an aortic arch, an aorta (descending aorta), an iliac artery, and the like.

Second Embodiment

Figure 11:
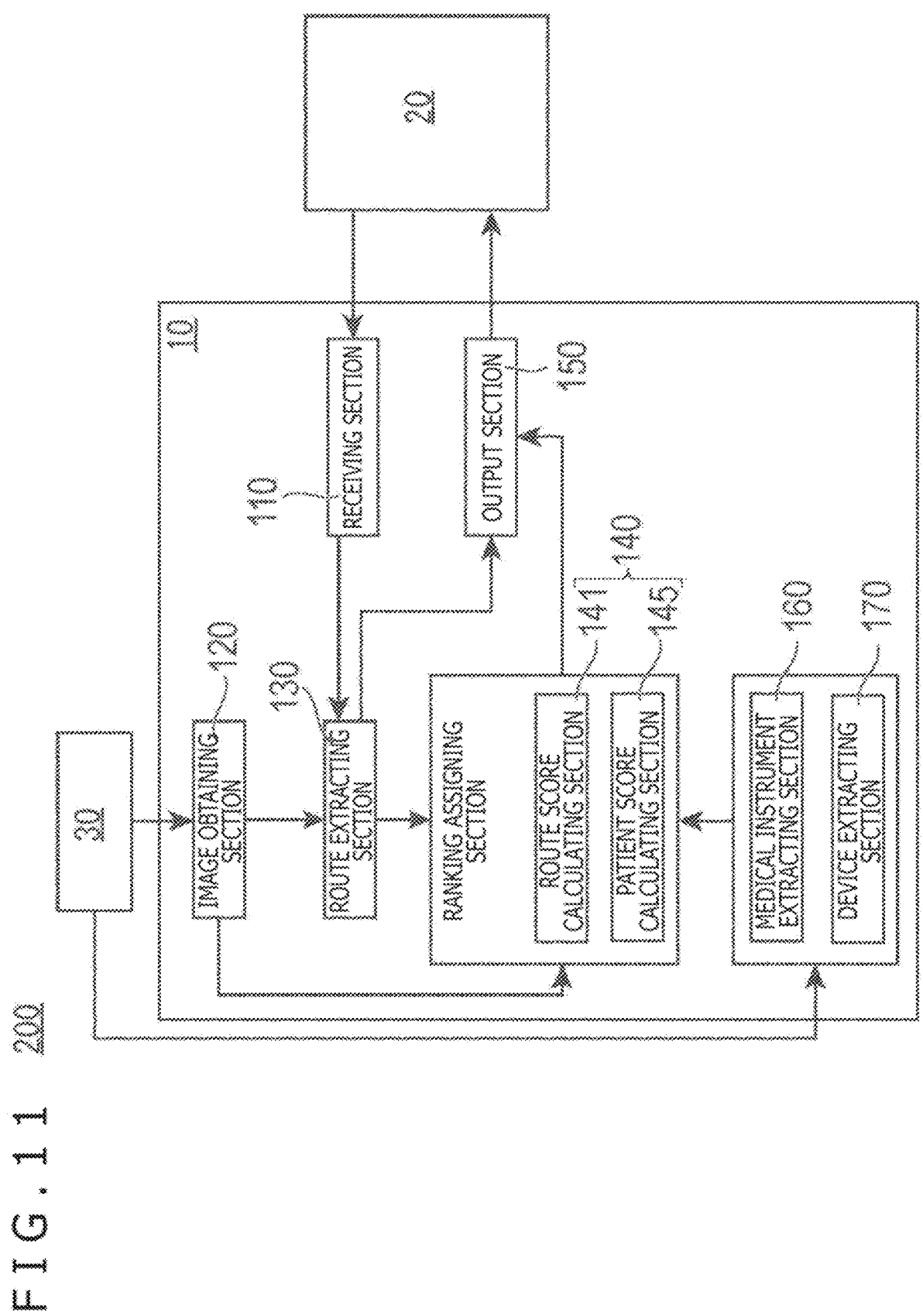
FIG. 11 is a block diagram depicting a functional configuration of a route selection assistance system according to a second embodiment.

Referring to FIG. 11, a route selection assistance system 200 according to a present embodiment includes a medical instrument extracting section 160 that extracts a kind (i.e., type) of medical instrument to be used for a procedure and a device extracting section 170 that extracts useable device candidates according to the kind of medical instrument extracted by the medical instrument extracting section 160, in addition to the functional configuration of the route selection assistance system 1 according to the foregoing embodiment.

The route selection assistance system 200 according to the present embodiment will be described in the following. In accordance with an exemplary embodiment, a device configuration of the route selection assistance system 200 according to the present embodiment is the same as the device configuration of the route selection assistance system 1 according to the foregoing embodiment. A functional configuration of the route selection assistance system 200 according to the present embodiment is the same as the functional configuration of the route selection assistance system 1 according to the foregoing embodiment except that the functional configuration of the route selection assistance system 200 according to the present embodiment further includes the medical instrument extracting section 160 and the device extracting section 170. The same devices and functional blocks as in the route selection assistance system 1 according to the foregoing embodiment are identified by the same reference numerals, and description of the same devices and functional blocks as in the route selection assistance system 1 will be omitted.

Referring to FIG. 12, the receiving section 110 receives an input of procedure information specifying a kind (i.e., type) of procedure to be performed by delivering a medical instrument to the target site RG via a blood vessel BV (corresponding to a living body lumen). The kinds of procedure can be, for example, expansion of a constriction in the blood vessel BV, excavation of the constriction of the blood vessel BV, imaging of the inside region BVa1 of the blood vessel BV, or releasing of a drug within the blood vessel BV. Except for receiving an input of procedure information, functions of the receiving section 110 are the same as the functions of the receiving section 110 in the route assistance system according to the foregoing embodiment.

In accordance with an exemplary embodiment, the medical instrument extracting section 160 extracts one or a plurality of kinds of medical instruments to be used for the kind of procedure specified by the procedure information. The kinds of medical instruments can be, for example, an introducer sheath, a guide wire, an imaging catheter, a micro-catheter, an angiographic catheter, a guide wire support catheter, a guiding catheter, a balloon catheter, a balloon-expandable stent, a self-expandable stent, a drug releasing stent, a drug releasing balloon, a directional coronary atherectomy (DCA) catheter, a microdissection catheter, a laser ablation catheter, and a catheter for image diagnosis.

In accordance with an exemplary embodiment, the catheter for image diagnosis, can be, for example, a catheter for obtaining an image by using an intravascular ultrasound diagnosis method (IVUS) or an optical coherence tomography diagnosis method (OCT).

In accordance with an exemplary embodiment, the device extracting section 170 extracts a useable device candidate for each kind of medical instrument extracted by the medical instrument extracting section 160. The device extracting section 170 extracts the useable device candidate on the basis of the presence or absence (i.e., availability) of stock of a device.

In a case where there are a plurality of useable device candidates, the device extracting section 170 extracts the plurality of device candidates within a range not exceeding an upper limit number. Though not particularly limited, the upper limit number can be, for example, about 10.

In a case where there is no useable device, the number of device candidates extracted by the device extracting section 170 is zero.

Referring to FIGS. 13A to 13C, the external server 30 stores a medical instrument list LS2 recording kinds of medical instruments to be used for each kind of procedure, a device list LS3 recording device candidates for each kind of medical instrument, and a device information list LS4 recording the presence or absence of stock of a device for each device candidate.

In accordance with an exemplary embodiment, the device list LS3 records commercially available devices for each kind of medical instrument. The devices can be, for example, identified by unique device identifiers. The unique device identifiers can be, for example, the manufacturer name of a manufacturer selling devices, a model name, a pharmaceutical approval number, a product code, bar code data, a product name, and a lot number.

In accordance with an exemplary embodiment, the device information list LS4 records the presence or absence of stock of devices in a facility in which the route selection assistance system 200 is used. In accordance with an exemplary embodiment, the device information list LS4 can be updated so that the recorded information is maintained to be latest information.

In accordance with an exemplary embodiment, the medical instrument extracting section 160 extracts kinds of medical instruments by using the medical instrument list LS2. The device extracting section 170 extracts useable device candidates by using the device list LS3 and the device information list LS4.

In accordance with an exemplary embodiment, the ranking assigning section 140 adjusts rankings assigned to the plurality of routes RT extracted by the route extracting section 130 on the basis of a result of the device extraction by the device extracting section 170.

In accordance with an exemplary embodiment, the ranking assigning section 140 decreases the ranking of a route RT for which no useable device is extracted in the device extracting section 170.

Referring to FIG. 14, the output section 150 outputs the device candidates extracted by the device extracting section 170 to the display 20 in addition to information output by the output section 150 of the route selection assistance system 1 according to the foregoing embodiment.

In accordance with an exemplary embodiment, the output section 150 may display information identifying a site having a largest bending degree P (which site will hereinafter be a maximum bending site) in which site a device causes, for example, a kink or the like, and it is thus expected to be difficult for the device to pass (which information is for example the name of the site of the blood vessel BV) and a numerical value indicating a degree of bending such as a curvature, an angle (angle θ to be described later with reference to FIG. 22, or the like), at the site. The output section 150 can perform processing of displaying these on the basis of the bending degree P calculated by the bending degree calculating section 144.

In addition, the output section 150 may display not only the maximum bending site but also information identifying other sites and degrees of bending in order of the magnitude of the bending degree P.

As for a device expected to have difficulty in passing through the maximum bending site, in accordance with an exemplary embodiment, the ranking of the device in the route RT can be decreased.

The output section 150 outputs, to the display 20, the routes RT, the rankings, the route scores SR, and the patient scores SP in order to assist an operator, for example, a doctor in selecting a device to be used for a procedure performed by delivering a medical instrument to the target site RG within the living body BD via the blood vessel BV.

According to the route selection assistance system 200, the recording medium on which a route selection assistance program is recorded, and the route selection assistance method in accordance with the present embodiment, the receiving section 110 receives an input of procedure information specifying a kind of procedure to be performed by delivering a medical instrument via the blood vessel BV. In accordance with an exemplary embodiment, the route selection assistance system 200 according to the present embodiment includes the medical instrument extracting section 160 that extracts kinds of medical instruments to be used for the procedure specified by the procedure information and the device extracting section 170 that extracts useable device candidates for each kind of medical instrument extracted by the medical instrument extracting section 160. The output section 150 then outputs a result of the extraction of the device candidates by the device extracting section 170. Thus, the operator can rather easily select a device to be used for a procedure performed by delivering a medical instrument via the blood vessel BV. Therefore, a relative burden on the operator at a time of performing a procedure by delivering a medical instrument via the blood vessel BV can be reduced.

First Modification of Second Embodiment

In the foregoing second embodiment, the device extracting section 170 extracts useable device candidates on the basis of the presence or absence of stock of devices. However, the device extracting section 170 may extract useable device candidates using characteristics of devices.

In the route selection assistance system according to the present modification, the device extracting section 170 includes a device characteristic information obtaining section (not shown) that obtains device characteristic information recording the characteristics of devices.

Referring to FIG. 15, the device information list LS4 according to the present modification records device characteristic information for each device.

The device characteristic information obtaining section obtains the device information list LS4 stored in the external server 30 via the network. The device characteristic information obtaining section obtains the device characteristic information from the device information list LS4.

In accordance with an exemplary embodiment, the device extracting section 170 includes a device ranking assigning section (not shown) that assigns rankings to devices on the basis of the device characteristic information obtained by the device characteristic information obtaining section, and extracts a device whose ranking assigned by the device ranking assigning section is equal to or more than a predetermined threshold value as a useable device candidate. Though not particularly limited, the threshold value can be, for example, 10.

The device characteristic information includes device scores obtained by indexing dynamic performance of the devices.

The dynamic performance of the devices can be, for example, stiffness, pushability, trackability, slidability, kink-resistant performance, or the like.

The dynamic performance of the devices may differ depending on a kind of medical instrument. For example, in the case of a guide wire, indexing may be performed by using stiffness, and in the case of a guiding catheter, indexing may be performed by using pushability and trackability or kink-resistant performance.

In accordance with an exemplary embodiment, the device ranking assigning section assigns rankings to the devices in decreasing order of the device scores.

The output section 150 outputs the rankings assigned by the device extracting section 170.

According to the route selection assistance system, the recording medium on which the route selection assistance program is recorded, and the route selection assistance method in accordance with the present modification, the device extracting section 170 includes the device characteristic information obtaining section that obtains the device characteristic information recording the characteristics of devices. The device extracting section 170 extracts useable device candidates by using the device characteristic information. The operator can therefore rather easily select a device in consideration of the characteristics of the devices.

In addition, according to the route selection assistance system, the recording medium on which the route selection assistance program is recorded, and the route selection assistance method in accordance with the present modification, the device extracting section 170 extracts useable device candidates by using device scores obtained by indexing the dynamic performance of devices. The operator can therefore rather easily select a device in consideration of the dynamic performance of the devices.

Second Modification of Second Embodiment

Further, the device extracting section 170 may extract useable device candidates by using characteristics of the target site RG.

In a route selection assistance system according to a present modification, the route extracting section 130 includes a target site analyzing section (not shown) that analyzes the characteristics of the target site RG by using the imaging image of the blood vessel BV.

Referring to FIG. 16, the target site analyzing section identifies a lesion site N in the target site RG, and measures the length of the identified lesion site N.

Using the imaging image of the blood vessel BV, the target site analyzing section identifies, as the lesion site N, a part where a distance H between an inner wall Vw1 of the blood vessel BV and an outer wall Vw2 of the blood vessel BV is larger than a predetermined threshold value.

In accordance with an exemplary embodiment, the target site analyzing section measures the length of the identified lesion site N using the imaging image of the blood vessel BV.

The device characteristic information according to the present modification records the length of a procedure part M for performing a procedure on the lesion site N in a device. For example, in a case where a kind of medical instrument is a balloon catheter, the length of the procedure part M is the length of a balloon.

The device extracting section 170 extracts, as a useable device, a device whose procedure part M has a larger length than the length of the lesion site N which length is measured by the target site analyzing section.

According to the route selection assistance system, the recording medium on which the route selection assistance program is recorded, and the route selection assistance method in accordance with the present modification, the route extracting section 130 includes the target site analyzing section that analyzes the characteristics of the target site RG by using the imaging image of the blood vessel BV. The device extracting section 170 extracts useable device candidates by using a result of the analysis of the target site analyzing section and the device characteristic information. The operator can therefore rather easily select an appropriate device according to the characteristics of the target site RG.

In accordance with an exemplary embodiment, in a case where the lesion site N is a constriction, the target site analyzing section may calculate a constriction degree of the constriction (degree of clogging of the blood vessel BV at the constriction), whether there is chronic total occlusion (CTO), and the hardness of the constriction in the case of chronic total occlusion. The device extracting section 170 may then extract useable devices using the constriction degree or the like calculated by the target site analyzing section.

In addition, in the case where a device is a balloon catheter, for example, the device characteristic information may record an expansion diameter of a balloon, a nominal pressure (NP), a rated burst pressure (RBP), information distinguishing between semi-compliance or non-compliance, or the like.

The target site analyzing section may identify the length of the lesion site N and the constriction degree of a constriction or the like in the case where the lesion site N is the constriction by a publicly known numerical analysis method such as computational fluid dynamics (CFD) by using a flow rate, blood pressure, or the like of blood in the vicinity of the lesion site N. Modeling of the blood vessel BV in a case where computational fluid dynamics is applied can be performed by using the imaging image of the blood vessel BV.

Third Modification of Second Embodiment

The device extracting section 170 may output non-extraction reason information recording a reason for not being extracted as a useable device candidate via the output section 150.

In accordance with an exemplary embodiment, the non-extraction reason information records a reason for not being extracted as a useable device candidate for each device. A reason for not being extracted as a useable device candidate is for example "no stock," (i.e., the device is not currently available), "commercially available only in foreign countries (overseas)," "pending pharmaceutical application (waiting for approval of a public institution which approval is required in selling of a medical instrument," "lacking in stiffness," "insufficient length of the procedure part as compared with the length of the lesion site," "fear of occurrence of a kink in the maximum bending site," or the like.

In accordance with an exemplary embodiment, by referring to the non-extraction reason information, a device manufacturer, for example, can more appropriately perform adjustment of a shipment of the device, an improvement of the dynamic performance of the device, an improvement of the shape of the procedure part M of the device, and the like.

Third Embodiment

Figure 17:
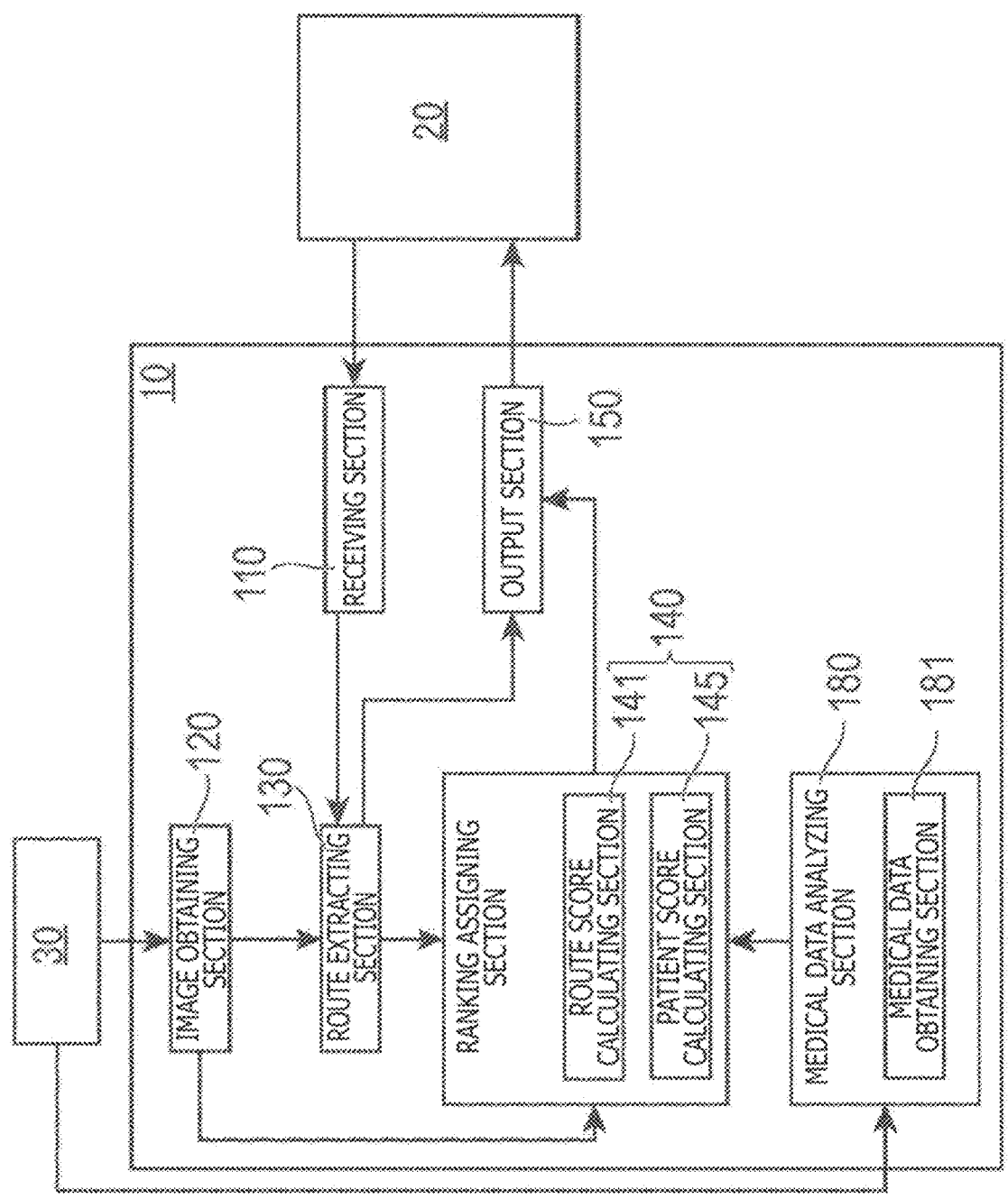
FIG. 17 is a block diagram showing a functional configuration of a route selection assistance system according to a third embodiment.

Referring to FIG. 17, a route selection assistance system 300 according to a present embodiment includes a medical data analyzing section 180 that analyzes medical data used in a medical field in addition to the functional configuration of the route selection assistance system 1 according to the foregoing first embodiment. The ranking assigning section 140 adjusts rankings using a result of the analysis of the medical data analyzing section 180.

The route selection assistance system 300 according to the present embodiment will be described in the following. In accordance with an exemplary embodiment, a device configuration of the route selection assistance system 300 according to the present embodiment is the same as the device configuration of the route selection assistance system 1 according to the foregoing embodiment. A functional configuration of the route selection assistance system 300 according to the present embodiment is the same as the functional configuration of the route selection assistance system 1 according to the foregoing embodiment except that the functional configuration of the route selection assistance system 300 according to the present embodiment further includes the medical data analyzing section 180. The same devices and functional blocks as in the route selection assistance system according to the foregoing embodiment are identified by the same reference numerals, and description of the same devices and functional blocks as in the route selection assistance system will be omitted.

The medical data analyzing section 180 includes a medical data obtaining section 181 that obtains medical data used in a medical field.

The medical data includes procedure history information that, for each procedure of delivering a medical instrument to a site within the living body BD via the blood vessel BV, records the characteristics of a route RT selected in the procedure and the characteristics of routes RT not selected in the procedure. The characteristics of the routes RT which characteristics are recorded in the procedure history information may for example be recorded as structured data such as the lengths of the routes RT and the bending degrees of the routes RT, or may be recorded as data not structured such as image data. In addition, the medical data may include data released by a society or the like.

For each of the plurality of routes RT extracted by the route extracting section 130, the medical data analyzing section 180 calculates a degree of possibility of the route RT being selected by the operator who is to deliver a medical instrument to a site within the living body BD via the blood vessel BV.

In accordance with an exemplary embodiment, the medical data analyzing section 180 calculates the degree of possibility of the route RT being selected by analyzing the procedure history information. Though not particularly limited, a machine learning method using an artificial neural network (ANN), for example, can be applied as a method of analyzing the procedure history information.

Figure 18:
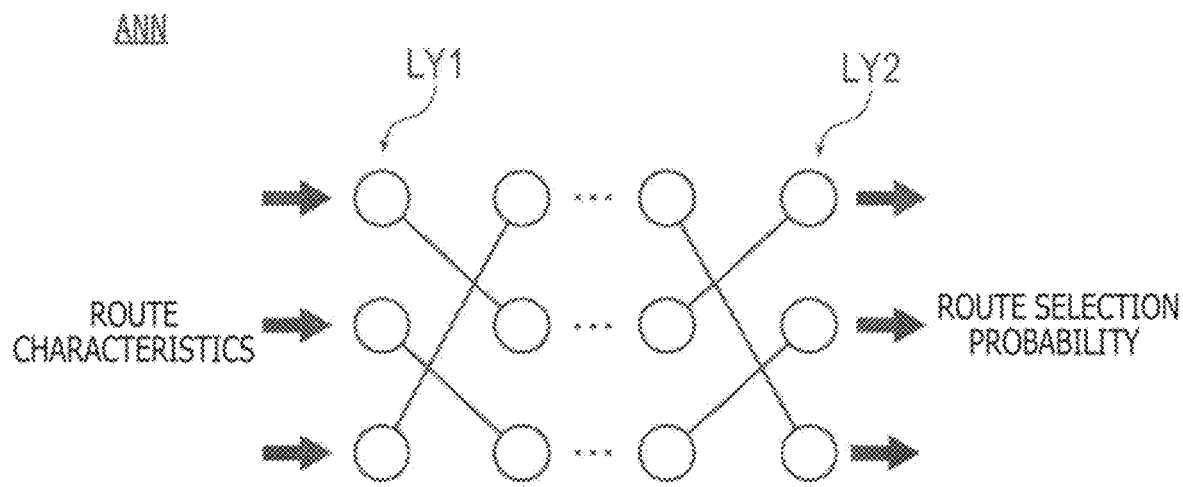
FIG. 18 is a diagram schematically showing an artificial neural network used by a medical data analyzing section of the route selection assistance system according to the third embodiment.

Referring to FIG. 18, in the case of the machine learning method using ANN, the characteristics of the route RT of the blood vessel BV (the length of the route RT, the bending degree of the route RT, and the like) are input to an input layer LY1. A probability of the operator selecting the route RT of the blood vessel BV which route has the input characteristics is output to an output layer LY2. The output probability may be a continuous numerical value, or may be a discrete value, for example, such as "high," "medium," or "low."

The medical data analyzing section 180 obtains the probability of the route RT being selected by the operator by inputting the characteristics of the route RT extracted by the route extracting section 130 to ANN learned by using the procedure history information.

The ranking assigning section 140 adjusts the rankings assigned to the plurality of routes RT extracted by the route extracting section 130 on the basis of the degrees of possibility of the routes RT being selected, the degrees of possibility being calculated by the medical data analyzing section 180.

In accordance with an exemplary embodiment, the ranking assigning section 140 calculates an operator score SD determined according to the degree of possibility of the route RT being selected. The ranking assigning section 140 assigns rankings to the plurality of routes RT extracted by the route extracting section 130 in increasing order of a value SR×SP/SD obtained by dividing a product of the route score SR and the patient score SP by the operator score SD.

For example, from the characteristics of a first route RT having a radial artery as the introduction site RS (that is, a route in TRI) and the characteristics of a second route RT having a femoral artery as the introduction site RS (that is, a route in TFI), when the probability calculated by the medical data analyzing section 180 for the first route RT is higher than the probability calculated by the medical data analyzing section 180 for the second route RT, the ranking assigning section 140 calculates that the operator score SD of the first route RT is higher than the operator score SD of the second route RT. Consequently, as compared with the case of the first embodiment in which a ranking is assigned by using only the route score SR and the patient score SP, the ranking assigning section 140 in the present embodiment adjusts the ranking of the first route RT to a relatively high side, and adjusts the ranking of the second route RT to a relatively low side.

In accordance with an exemplary embodiment, this means that a conventional process in which the operator, for example, a doctor determines whether to select TRI or to select TFI in consideration of the characteristics of the first route RT and the characteristics of the second route RT is performed by the above-described ranking adjustment in the ranking assigning section 140. Therefore, according to the route selection assistance system in accordance with the present embodiment, the operator such as a doctor can rather easily select a more appropriate route.

According to the route selection assistance system 300, the recording medium on which the route selection assistance program is recorded, and the route selection assistance method in accordance with the present embodiment, the medical data analyzing section 180 analyzing the medical data is included. For each of the plurality of routes RT extracted by the route extracting section 130, the medical data analyzing section 180 calculates an operator score SD determined according to the possibility of the route RT being selected by the operator who is to deliver a medical instrument to a site within the living body BD via the blood vessel BV. The ranking assigning section 140 then adjusts rankings assigned to the plurality of routes RT extracted by the route extracting section 130 on the basis of the operator scores SD calculated by the medical data analyzing section 180. Thus, the operator can select a route RT according to the characteristics of the route RT of the blood vessel BV rather easily.

In accordance with an exemplary embodiment, the medical data is not particularly limited as long as the medical data is data used in the medical field. The medical data can include information on a procedure performed in the past in the facility in which the route selection assistance system 300 is used and/or information on a procedure performed in the past in a facility other than the facility in which the route selection assistance system 300 is used. The medical data can be a part or whole of data stored in a management system (a medical image management system (PACS), a radiology information system (RIS), a hospital information system (HIS), and the like) installed in the facility in which the route selection assistance system 300 is used. The medical data analyzing section 180 can obtain the medical data from the above-described management system. The medical data can include information recorded in electronic medical records (EMR).

In addition, a method of analyzing the medical data may be a deep learning method using an artificial neural network, or may be a statistical analysis technology.

In addition, the medical data analyzing section 180 may make a part of the functions of the medical data analyzing section 180 be executed by an external server, and obtain a result of the execution from the external server.

In addition, the ranking assigning section 140 may make the medical data analyzing section 180 analyze the medical data, and calculate the magnitude of a burden on the patient using a result of the analysis of the medical data analyzing section 180.

Modification of Third Embodiment

In accordance with an exemplary embodiment, the probability calculated by the medical data analyzing section 180 in the foregoing third embodiment is a degree of possibility of the route RT being selected by an ordinary operator. However, the medical data analyzing section 180 may calculate a degree of possibility of the route RT being selected, for example, by a specific operator.

A route selection assistance system according to a present modification includes an operator mode in which candidates for a route RT suitable for a specific operator assisted in route selection are output. The medical data analyzing section 180 calculates a degree of possibility of the route RT being selected by the specific operator in the operator mode.

The receiving section 110 receives operator identification information identifying the operator who uses the route selection assistance system.

In accordance with an exemplary embodiment, the medical data includes, for each procedure of delivering a medical instrument to a site within the living body BD via the blood vessel BV, specific history information recording the characteristics of a route RT selected by the operator identified by the operator identification information in the procedure and the characteristics of routes RT not selected by the operator identified by the operator identification information in the procedure.

Using the specific history information, the medical data analyzing section 180 calculates, as a degree of possibility of the route RT being selected, a degree of possibility of the route RT being selected by the specific operator identified by the operator identification information.

The route selection assistance system, the recording medium on which the route selection assistance program is recorded, and the route selection assistance method in accordance with the present modification output candidates for a route RT suitable for a specific operator assisted in route selection. Thus, the operator can rather easily select an appropriate route RT from among the plurality of routes RT of blood vessels BV through which a medical instrument can be delivered to the target site RG.

In accordance with an exemplary embodiment, the specific history information is not particularly limited as long as the specific history information is information related to the operator identified by the operator identification information. For example, the specific history information can include kinds of cases and the number of times of procedures handled by the operator identified by the operator identification information.

In addition, the route selection assistance system may retain the operator identification information received by the receiving section 110. Thus, once the operator inputs the operator identification information, the operator can receive an output of candidates for the route RT suitable for the operator without thereafter inputting the operator identification information.

In accordance with an exemplary embodiment, the specific operator in the operator mode is not limited to an operator actually assisted in route selection, but may, for example, be an operator distinguished in the procedure of TRI or the like. In this case, the operator using the route selection assistance system according to the present modification can rather easily select a more appropriate route by tracing the thinking of route selection of the distinguished operator.

First Other Modification

Figure 19:
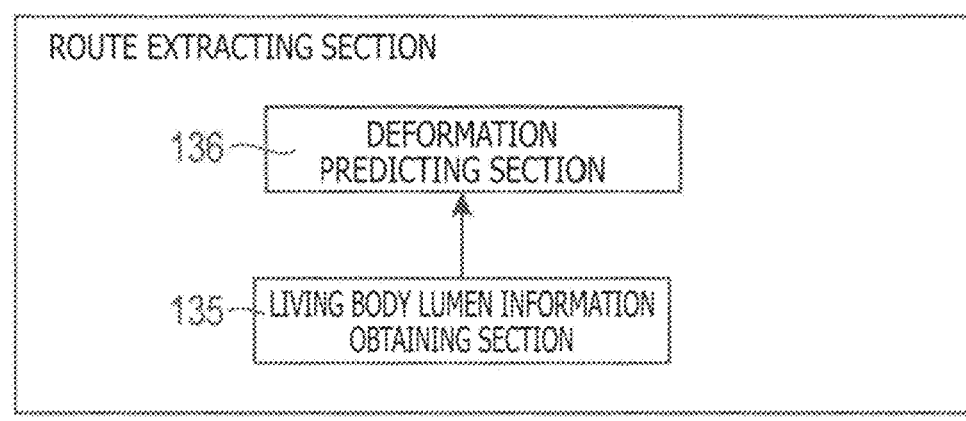
FIG. 19 is a block diagram showing a functional configuration of a route extracting section of a route selection assistance system according to a first modification.

Referring to FIG. 19, the route extracting section 130 may include a living body lumen characteristic information obtaining section 135 that obtains information related to dynamic characteristics of the blood vessel BV and a deformation predicting section 136 that predicts a deformation of the blood vessel BV at a time of delivering a medical instrument to the blood vessel BV. The route score calculating section 141 may adjust a calculated route score SR by using a result of the prediction of the deformation predicting section 136.

The living body lumen characteristic information obtaining section 135 obtains information related to the dynamic characteristics of the blood vessel BV.

The information related to the dynamic characteristics of the blood vessel BV can include information related to hardness of the blood vessel BV. The information related to the hardness of the blood vessel BV is information recording the hardness of the blood vessel BV at each site of the blood vessel BV. The hardness of the blood vessel BV can, for example, be measured for each site of the blood vessel BV by any suitable measuring method such as a pulse wave velocity (PWV) measuring method. When the hardness of the blood vessel BV is measured by using PWV measuring method, the hardness of the blood vessel BV is expressed by a value indexed on the basis of a pulse wave velocity. In addition, an augmentation index (AI) measured by a publicly known method may be used as the hardness of the blood vessel BV. In addition, the hardness of the blood vessel BV may be identified from a blood pressure and the flow rate and flow velocity of blood by using any suitable numerical analysis method such as computational fluid dynamics.

Further, the medical data analyzing section may analyze medical data recording the hardness of blood vessels BV, blood pressures, blood flow rates and blood flow velocities, and the like of a plurality of patients so that the hardness of the blood vessel BV of the target patient is derived from the blood pressure, blood flow rate and blood flow velocity, and the like of the target patient. In this case, any suitable machine learning (deep learning) method or a statistical method can be used as a method of the analysis of the medical data analyzing section.

Figure 20A:
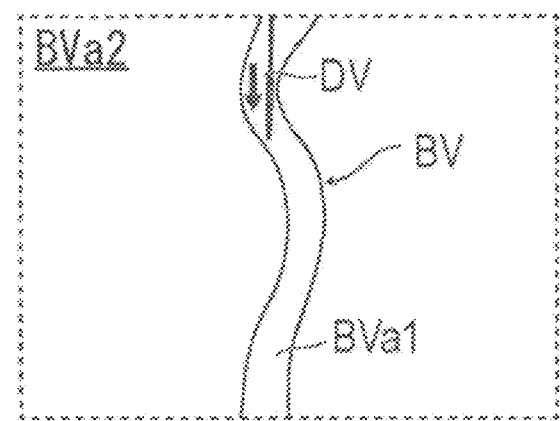
FIGS. 20A and 20B are diagrams of assistance in explaining functions of a deformation predicting section of the route selection assistance system according to the first modification, wherein FIG. 20A being a schematic diagram showing the shape of a blood vessel before a deformation is predicted by the deformation predicting section, and FIG. 20B being a schematic diagram showing the shape of the blood vessel after the deformation predicted by the deformation predicting section.
Figure 20B:
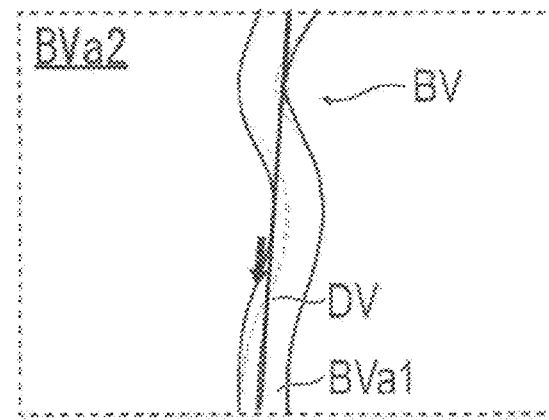

Referring to FIGS. 20A and 20B, the deformation predicting section 136 predicts a deformation of the blood vessel BV at a time of delivering a medical instrument to the blood vessel BV by using living body lumen characteristic information obtained by the living body lumen characteristic information obtaining section 135.

The deformation predicting section 136 predicts a deformation of the blood vessel BV at a time of delivering a representative device DV having typical dynamic performance of the medical instrument through the blood vessel BV. A method of predicting the deformation of the blood vessel BV is not particularly limited, and any suitable dynamic numerical simulation method or the like can be used.

In accordance with an exemplary embodiment, the route length calculating section 143 corrects the length of a route RT according to a result of the prediction of the deformation of the blood vessel BV which deformation is predicted by the deformation predicting section 136. The bending degree calculating section 144 corrects the bending degree P of the route RT according to the result of the prediction of the deformation of the blood vessel BV which deformation is predicted by the deformation predicting section 136.

According to the route selection assistance system, the recording medium on which the route selection assistance program is recorded, and the route selection assistance method in accordance with the present modification, the route score calculating section 141 can calculate the route scores SR with higher accuracy. Therefore, the operator can rather easily select a more appropriate route RT from among the plurality of routes RT of blood vessels BV through which a medical instrument can be delivered to the target site RG in consideration of the ease of delivery of the medical instrument at a time of delivery of the medical instrument.

In accordance with an exemplary embodiment, the deformation predicting section 136 may predict a deformation of the blood vessel BV by using experimental data of a model experiment related to the deformation of the blood vessel BV, the model experiment using an actually existing device. The experimental data can record an experiment result (result of deformation of the blood vessel BV) for each of one or a plurality of devices having a possibility of being used as a device to be delivered to the target site RG via the blood vessel BV.

In this case, for example, the deformation predicting section 136 may predict a deformation of the blood vessel BV by using the experimental data of a device having a highest ranking assigned by the device ranking assigning section among the devices extracted by the device extracting section 170.

In addition, the experimental data may record the length and diameter of the device, the bending stiffness and modulus of elasticity of each part constituting the device, or the like. When the experiment result of the device used for predicting the deformation of the blood vessel BV is not included in the experimental data, the deformation of the blood vessel BV may be predicted by using the experimental data of a similar device in terms of the length and diameter of the device, the bending stiffness and modulus of elasticity of each part constituting the device, or the like. Alternatively, a representative device may be selected in advance, and the deformation of the blood vessel BV may be predicted by using the experimental data of the representative device.

Further, the deformation predicting section 136 may determine whether or not the deformation of the blood vessel BV can be predicted on the basis of the experimental data of a model experiment, and the output section 150 may output a result of the determination of the deformation predicting section 136 as to whether or not the deformation of the blood vessel BV can be predicted.

Second Other Modification

Further, the ranking assigning section 140 may output basis information FR recording a basis of ranking assignment via the output section 150. In accordance with an exemplary embodiment, the basis information FR can include route score basis information recording a basis of calculating a route score SR.

The route score basis information can be, for example, information that, for each site of the blood vessel BV constituting the route RT, records a bending degree P before correction is performed according to a result of prediction of a deformation of the blood vessel BV which deformation is predicted by the deformation predicting section 136 and a bending degree P after the correction is performed.

Figure 21A:
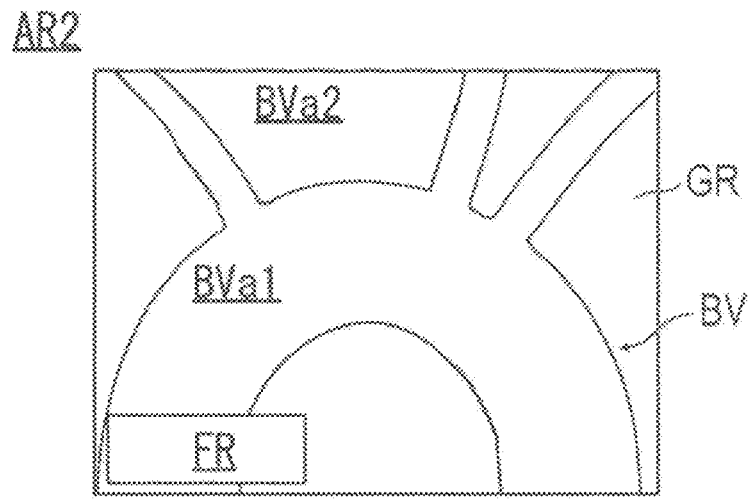
FIGS. 21A-21C are diagrams of assistance in explaining functions of an output section of a route selection assistance system according to a second modification, FIG. 21A being a schematic diagram showing a display displaying reason information with regard to an aortic arch, FIG. 21B being a schematic diagram showing the display displaying reason information with regard to a descending aorta, and FIG. 21C being a schematic diagram showing the display displaying reason information with regard to an iliac artery.
Figure 21B:
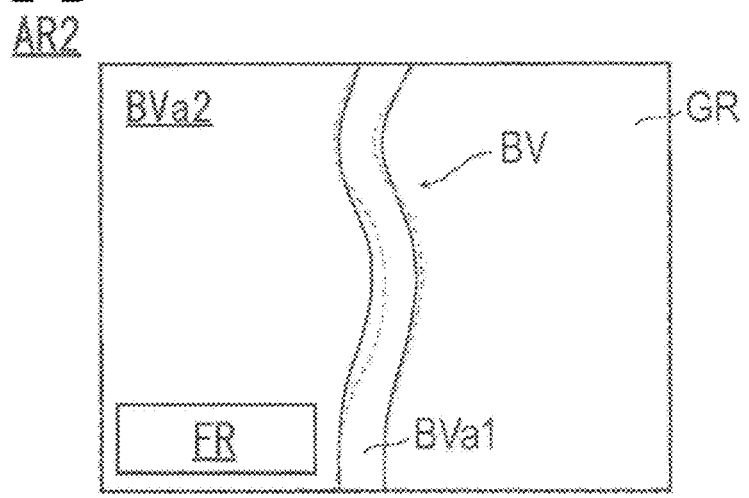
Figure 21C:
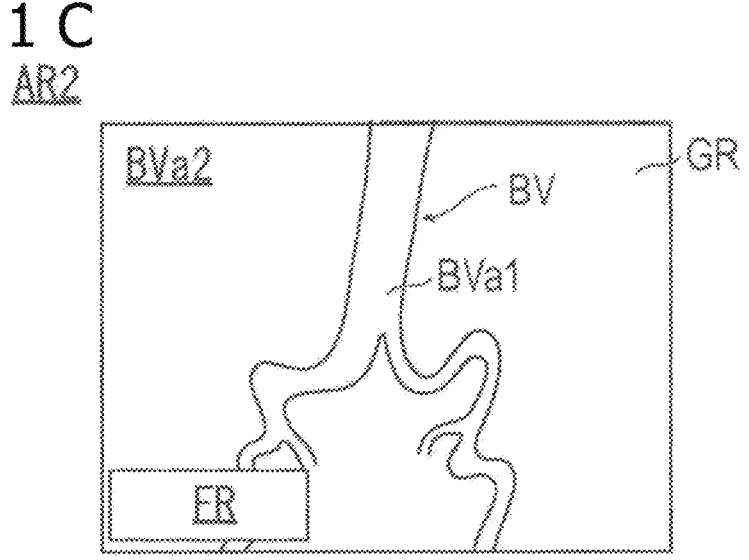

Referring to FIGS. 21A, 21B, and 21C, the output section 150 may display the basis information FR for each site of the blood vessel BV constituting the route RT in a detailed display region AR2 of the display 20.

By referring to the basis information FR output by the output section 150, the operator can rather easily verify whether or not one route RT selected from among the plurality of routes RT of blood vessels BV through which a medical instrument can be delivered to the target site RG is an appropriate route RT.

For example, when the operator determines that the bending degree P after correction is performed for the one route RT selected from among the plurality of routes RT is not an appropriate value on the basis of own experience of the operator, the operator can select another route RT different from the one route RT.

In accordance with an exemplary embodiment, the basis information FR is not limited to information about the correction of the bending degree P. For example, the basis information FR may be information indicating that a ranking is assigned with priority given to a burden on the blood vessel BV over an invasion degree because the target patient is elderly, that a ranking is lowered because there is no stock of a useable device (i.e., the device is not available), or that the ranking of a route RT having a high probability of being selected by another operator is increased.

In accordance with an exemplary embodiment, the operator can relatively accurately verify whether or not the selected one route RT is an appropriate route RT in consideration of the basis information FR, a result of selection of a route by another operator, data released by a society, and the like.

Third Other Modification

In the foregoing embodiments and the modifications of the foregoing embodiments, the bending degree calculating section 144 calculates, for each vertex PP of the center line CL of the blood vessel BV, the curvature of the center line CL at the vertex PP, and calculates, as the bending degree P, a sum of curvatures calculated for the respective vertices PP. However, a method of calculating the bending degree P in the bending degree calculating section 144 is not particularly limited.

Figure 22A:
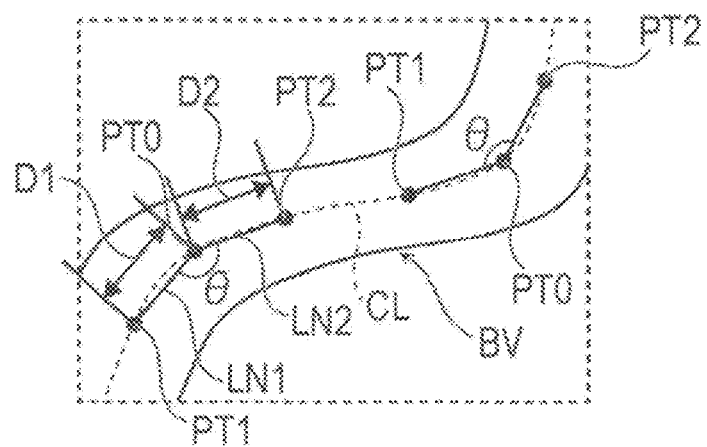
FIG. 22A is a schematic diagram of assistance in explaining a bending degree calculating method in a route selection assistance system according to a third modification.

For example, referring to FIG. 22A, the bending degree calculating section 144 may calculate, as the bending degree P, a sum of an angle θ between straight lines LN1 and LN2 obtained by connecting one point PT0 on the center line CL derived by the center line deriving section 142 to two arbitrary points PT1 and PT2 on the center line CL which points are adjacent to the one point PT0. In this case, the point PT1 is separated from the point PT0 by a predetermined distance D1 in one direction along the center line CL, and the point PT2 is separated from the point PT0 by a predetermined distance D2 in another direction along the center line CL. The distance D1 and the distance D2 may be equal to each other, or may be different from each other. The magnitude of the distance D1 and the distance D2 is not particularly limited.

Figure 22B:
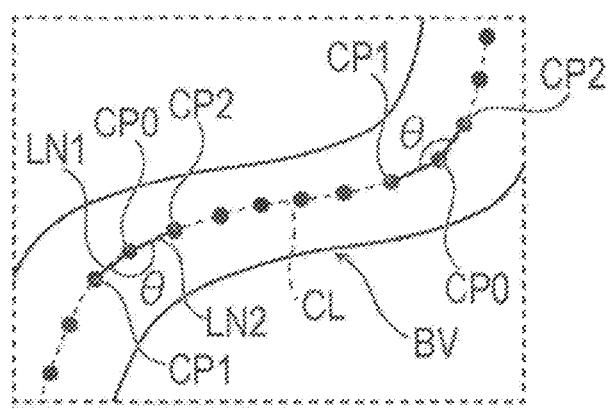
FIG. 22B is a schematic diagram of assistance in explaining another bending degree calculating method in the route selection assistance system according to the third modification.

In addition, referring to FIG. 22B, the bending degree calculating section 144 may calculate, as the bending degree P, a sum of an angle θ between straight lines LN1 and LN2 obtained by connecting one center CP0 of the blood vessel BV which center is discretely calculated by the center line deriving section 142 to two centers CP1 and CP2 adjacent to the one center CP0.

In accordance with an exemplary embodiment, the angle θ means an inferior angle of two angles (inferior angle and superior angle) formed by the straight line LN1 and the straight line LN2.

The route selection assistance system, the recording medium on which the route selection assistance program is recorded, and the route selection assistance method have been described above through embodiments and modifications of the embodiments. However, the present disclosure is not limited to only configurations described in the embodiments, but can be changed as appropriate on the basis of the description of claims.

For example, in the foregoing embodiments and the modifications of the foregoing embodiments, a blood vessel of a lower limb is illustrated as the target site. However, the target site is not particularly limited. For example, the target site may be a blood vessel in a brain, a heart, or the like. Further, in the foregoing embodiments and the modifications of the foregoing embodiments, description has been made by taking as an example a case where the living body lumen is a blood vessel. However, the living body lumen is not limited to a blood vessel, but may be a vessel, a bile duct, an oviduct, a hepatic duct, a trachea, an esophagus, a urethra, or the like.

In the foregoing embodiments and the modifications of the foregoing embodiments, the output section outputs, to the display, the plurality of routes extracted by the route extracting section, the rankings assigned by the ranking assigning section, the route scores, and the patient scores. However, the output section may output, as data, the plurality of routes extracted by the route extracting section, the rankings assigned by the ranking assigning section, the route scores, and the patient scores to the external server. In this case, the route of a living body lumen can be expressed as a set of coordinates with the target site as an origin.

In addition, in the foregoing embodiments and the modifications of the foregoing embodiments, the ranking assigning section 140 assigns rankings to the plurality of routes RT extracted by the route extracting section 130 in increasing order of the product SR×SP of the route score SR and the patient score SP. However, a method of ranking assignment using the route score SR and the patient score SP is not particularly limited. For example, the ranking assigning section 140 may assign rankings to the plurality of routes RT extracted by the route extracting section 130 in decreasing order of SR/SP, which is obtained by dividing the route score SR by the patient score SP. In this case, the rankings assigned by the ranking assigning section 140 are in decreasing order as viewed with respect to the route score SR, and are in increasing order as viewed with respect to the patient score SP.

In addition, in the foregoing embodiments and the modifications of the foregoing embodiments, the route score calculating section calculates a route score using the length of a route and the bending degree of the route. However, the route score calculating section may calculate the route score using the length of the route, the bending degree of the route, and/or the lumen size of the living body lumen constituting the route.

In addition, the route score calculating section may classify sites of the blood vessel constituting the route on the basis of forms of the sites, and calculate the route score using a result of the classification. For example, the route score calculating section may classify each site constituting the route into "difficult," "normal," "easy" from a viewpoint of a degree of difficulty in delivering a medical instrument on the basis of the form of the site, and calculate the route score using a result of the classification.

In addition, as illustrated in FIG. 20A and FIG. 20B, a device being delivered to the target site via the route of the blood vessel does not necessarily always pass through the center of the blood vessel. For example, in accordance with an exemplary embodiment, the route score calculating section may include a path predicting section that predicts a path in which the device passes in the blood vessel. In accordance with an exemplary embodiment, the route score calculating section may correct the calculated length of the route and the calculated bending degree of the route on the basis of the path predicted by the path predicting section.

In addition, in the foregoing embodiments and the modifications of the foregoing embodiments, the output section displays one of the plurality of routes extracted by the route extracting section on the display in response to a selection of the route which selection is received by the receiving section. However, the output section may simultaneously display the plurality of routes extracted by the route extracting section on the display. In this case, the output section may display the plurality of routes extracted by the route extracting section on the display in different colors.

In addition, in the foregoing embodiments and the modifications of the foregoing embodiments, the image information includes image data and supplementary information. However, it suffices for the image information to include at least image data of the living body lumen of the target patient, and the supplementary information is not an essential requirement.

In addition, the image data does not necessarily need to be divided for each site of the living body lumen. Even when the image data is not divided for each site of the living body lumen, the route extracting section can extract the route of the living body lumen through which a medical instrument can be delivered to the target site by using a publicly known image processing technology or the like on the basis of the image data.

In addition, in the foregoing embodiments and the modifications of the foregoing embodiments, the route selection assistance program recorded on the computer readable recording medium is read by the reading device and stored in the storage device, and thereby the route selection assistance system functions. However, the route selection assistance system may be provided in a state in which the route selection assistance program is stored in the storage device in advance. In addition, a part or all of the functions of the route selection assistance system may be implemented by a programmable circuit structure such as a field programmable gate array (FPGA) or the like. In this case, a part or the whole of the route selection assistance program is described in a hardware description language such as Verilog or the like.

In addition, in the foregoing embodiments and the modifications of the foregoing embodiments, the computer main unit and the display are configured as separate parts. However, the computer main unit and the display may be configured integrally with each other, or the display may be incorporated in the computer main unit.

In addition, in the foregoing embodiments and the modifications of the foregoing embodiments, the image obtaining section obtains image information from the external server. However, the image obtaining section may be configured by using an image photographing device for medical use, for example, an X-ray CT device, or an MRI device.

In addition, the medical data used in the foregoing third embodiment can be so-called big data including a large amount of structured data and/or unstructured data. The medical instrument extracting section and the device extracting section may extract kinds of medical instruments and devices by using the medical data.

In addition, the route extracting section, the medical instrument extracting section, and the device extracting section in the route selection assistance system may make the medical data analyzing section analyze the medical data, and extract routes, kinds of medical instruments, and devices by using a result of the analysis of the medical data analyzing section. For example, when there is no stock of devices belonging to a kind of medical instrument, the device extracting section may extract a device useable as a substitute by using the result of the analysis of the medical data analyzing section.

The detailed description above describes to a route selection assistance system assisting in selecting a route of a living body lumen for delivering a medical instrument to a site within a living body via the living body lumen, a recording medium on which a route selection assistance program is recorded, a route selection assistance method, and a diagnosis method. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A route selection assistance system for assisting in selecting a route of a living body lumen for delivering a medical instrument to a site within a living body via the living body lumen, the route selection assistance system comprising:
a receiving section configured to receive an input of site information specifying a target site within the living body as a target of delivering the medical instrument, wherein the receiving section is configured to receive an input of procedure information specifying a kind of procedure to be performed by delivering the medical instrument to the target site via the living body lumen;
an image obtaining section configured to obtain image information on an inside of the living body of a target patient as the target of delivering the medical instrument;
a route extracting section configured to extract a plurality of routes of the living body lumen, the plurality of routes allowing the medical instrument to be delivered to the target site, on a basis of the image information obtained by the image obtaining section;
a ranking assigning section including a route score calculating section configured to calculate, by using the image information obtained by the image obtaining section, route scores determined according to ease of delivery of the medical instrument at a time of delivery of the medical instrument via the routes and a patient score calculating section configured to calculate, by using the image information obtained by the image obtaining section, patient scores determined according to magnitude of a burden imposed on the target patient, the ranking assigning section assigning rankings to the plurality of routes extracted by the route extracting section by using the route scores and the patient scores;
an output section configured to output the plurality of routes extracted by the route extracting section and the rankings assigned by the ranking assigning section;
a medical instrument extracting section configured to extract kinds of medical instruments from a medical instrument list used for the procedure specified by the procedure information;
a device extracting section configured to extract a useable device candidate for each kind of medical instrument extracted by the medical instrument extracting section, and wherein the device extracting section includes a device characteristic information obtaining section configured to obtain device characteristic information recording a characteristic of a device, and extracts the useable device candidate by using the device characteristic information;
the ranking assigning section configured to adjust the rankings assigned to the plurality of routes extracted by the route extracting section on a basis of a result of extraction of the device candidate by the device extracting section;
the output section configured to output a result of extraction of the device candidate by the device extracting section;
the image information including an imaging image of the living body lumen; and
the route score calculating section configured to calculate the route scores using the imaging image.

2. The route selection assistance system according to claim 1, further comprising:
a medical data analyzing section that includes a medical data obtaining section configured to obtain medical data used in a medical field, and analyzes the medical data obtained by the medical data obtaining section;
wherein for each of the plurality of routes extracted by the route extracting section, the medical data analyzing section is configured to calculate a degree of possibility of the route being selected by an operator delivering the medical instrument to a site within the living body via the living body lumen; and
the ranking assigning section configured to adjust the rankings assigned to the plurality of routes extracted by the route extracting section on a basis of the degree of possibility that is calculated by the medical data analyzing section.

3. The route selection assistance system according to claim 1, further comprising:
a characteristic information obtaining section configured to obtain characteristic information recording a dynamic characteristic of the living body lumen;
a deformation predicting section configured to predict a deformation of the living body lumen at a time of delivering the medical instrument through the living body lumen by using the characteristic information obtained by the characteristic information obtaining section;
wherein the route score calculating section is configured to adjust the calculated route scores by using a result of prediction of the deformation predicting section.

4. The route selection assistance system according to claim 1, further comprising:
a patient information obtaining section configured to obtain patient information related to the target patient; and
wherein the patient score calculating section is configured to calculate the patient scores by using the patient information obtained by the patient information obtaining section.

5. The route selection assistance system according to claim 1, wherein
the output section includes a navigation section configured to guide a user through the routes extracted by the route extracting section.

6. A non-transitory computer readable recording medium on which a route selection assistance program assisting in selecting a route of a living body lumen for delivering a medical instrument to a site within a living body via the living body lumen is recorded, the route selection assistance program making a computer perform:
receiving an input of site information specifying a target site within the living body as a target of delivering the medical instrument;
obtaining image information on an inside of the living body of a target patient as a target of delivering the medical instrument, the image information including an imaging image of the living body lumen;
extracting a plurality of routes of the living body lumen, the plurality of routes allowing the medical instrument to be delivered to the target site, on a basis of the obtained image information;
calculating route scores determined according to ease of delivery of the medical instrument at a time of delivery of the medical instrument via the routes, calculating patient scores determined according to magnitude of a burden imposed on the target patient, and assigning rankings to the extracted plurality of routes by using the calculated route scores and the calculated patient scores;

outputting the extracted plurality of routes and the assigned rankings;

calculating the route scores by using the imaging image of the living body lumen when the route scores are calculated;

receiving an input of procedure information specifying a kind of procedure to be performed by delivering the medical instrument to the target site via the living body lumen;

extracting kinds of medical instruments from a medical instrument list used for the procedure specified by the procedure information;

extracting a useable device candidate for each kind of medical instrument extracted;

adjusting the rankings assigned to the plurality of routes extracted by the route extracting section on a basis of a result of extraction of the device candidate;

outputting a result of the extraction of the device candidate;

obtaining device characteristic information recording a characteristic of a device; and extracting the useable device candidate by using the device characteristic information.

7. The non-transitory computer readable recording medium according to claim 6, further comprising:

obtaining medical data used in a medical field;

analyzing the obtained medical data obtained;

calculating a degree of possibility of the route being selected by an operator delivering the medical instrument to a site within the living body via the living body lumen for each of the plurality of routes extracted; and adjusting the rankings assigned to the plurality of routes extracted by the route extracting section on a basis of the calculation of the degree of possibility of the route being selected by the operator delivering the medical instrument to the site.

8. The non-transitory computer readable recording medium according to claim 6, further comprising:

obtaining characteristic information recording a dynamic characteristic of the living body lumen;

predicting a deformation of the living body lumen at a time of delivering the medical instrument through the living body lumen; and adjusting the calculated route scores by using a result of the prediction of deformation of the living body lumen at the time of the delivering the medical instrument through the living body lumen.

9. The non-transitory computer readable recording medium according to claim 6, further comprising:

obtaining patient information related to the target patient; and calculating the patient scores by using the obtained patient information related to the target patient.

10. The non-transitory computer readable recording medium according to claim 6, comprising:

guiding an operator through the extracted routes.

11. A route selection assistance method of assisting in selecting a route of a living body lumen for delivering a medical instrument to a site within a living body via the living body lumen, the method comprising:

receiving an input of site information specifying a target site within the living body as a target of delivering the medical instrument;

obtaining image information on an inside of the living body of a target patient as the target of delivering the medical instrument, the image information including an imaging image of the living body lumen;

extracting a plurality of routes of the living body lumen, the plurality of routes allowing the medical instrument to be delivered to the target site, on a basis of the obtained image information;

calculating route scores determined according to ease of delivery of the medical instrument at a time of delivery of the medical instrument via the routes, calculating patient scores determined according to magnitude of a burden imposed on the target patient, and assigning rankings to the extracted plurality of routes by using the calculated route scores and the calculated patient scores;

outputting the extracted plurality of routes and the assigned rankings;

calculating the route scores by using the imaging image of the living body lumen when the route scores are calculated;

receiving an input of procedure information specifying a kind of procedure to be performed by delivering the medical instrument to the target site via the living body lumen;

extracting kinds of medical instruments from a medical instrument list used for the procedure specified by the procedure information;

extracting a useable device candidate for each kind of medical instrument extracted;

adjusting the rankings assigned to the plurality of routes extracted by the route extracting section on a basis of a result of extraction of the device candidate;

outputting a result of the extraction of the device candidate;

obtaining device characteristic information recording a characteristic of a device; and extracting the useable device candidate using the device characteristic information.

12. The method according to claim 11, further comprising:

obtaining medical data used in a medical field;

analyzing the obtained medical data obtained;

calculating a degree of possibility of the route being selected by an operator delivering the medical instrument to a site within the living body via the living body lumen for each of the plurality of routes extracted; and adjusting the rankings assigned to the plurality of routes extracted by the route extracting section on a basis of the calculation of the degree of possibility of the route being selected by the operator delivering the medical instrument to the site.

13. The method according to claim 11, further comprising:

obtaining characteristic information recording a dynamic characteristic of the living body lumen;

predicting a deformation of the living body lumen at a time of delivering the medical instrument through the living body lumen; and adjusting the calculated route scores by using a result of the prediction of deformation of the living body lumen at the time of the delivering the medical instrument through the living body lumen.

14. A diagnosis method for diagnosing a route of a living body lumen for delivering a medical instrument to a site within a living body via the living body lumen, the diagnosis method comprising:

receiving an input of site information specifying a target site within the living body as a target of delivering the medical instrument;

obtaining image information on an inside of the living body of a target patient as the target of delivering the medical instrument, the image information including an imaging image of the living body lumen;

extracting a plurality of routes of the living body lumen, the plurality of routes allowing the medical instrument to be delivered to the target site, on a basis of the obtained image information;

assigning rankings to the extracted plurality of routes by using route scores determined according to ease of delivery of the medical instrument at a time of delivery of the medical instrument via the routes and patient scores determined according to magnitude of a burden imposed on the target patient;

diagnosing the route from the extracted plurality of routes and the assigned rankings;

calculating the route scores by using the imaging image of the living body lumen when the route scores are calculated;

receiving an input of procedure information specifying a kind of procedure to be performed by delivering the medical instrument to the target site via the living body lumen;

extracting kinds of medical instruments from a medical instrument list used for the procedure specified by the procedure information kinds of medical instruments used for the procedure;

extracting a useable device candidate for each kind of medical instrument extracted;

adjusting the rankings assigned to the plurality of routes extracted by the route extracting section on a basis of a result of extraction of the device candidate;

outputting a result of the extraction of the device candidate;

obtaining device characteristic information recording a characteristic of a device; and extracting the useable device candidate using the device characteristic information.

* * * * *